(12) United States Patent
Tan et al.

(10) Patent No.: US 9,617,318 B2
(45) Date of Patent: Apr. 11, 2017

(54) **HETEROGENEOUS NUCLEAR RIBONUCLEOPROTEIN A2\* (HNRNP A2\*) AND NUCLEIC ACID ENCODING THE SAME**

(71) Applicant: INSTITUTE OF ZOOLOGY, CHINESE ACADEMY OF SCIENCES, Beijing (CN)

(72) Inventors: Zheng Tan, Beijing (CN); Yong Zhao, Beijing (CN); Feng Wang, Beijing (CN); Yuhua Hao, Beijing (CN)

(73) Assignee: INSTITUTE OF ZOOLOGY, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 15/352,507

(22) Filed: Nov. 15, 2016

(65) Prior Publication Data

US 2017/0058009 A1 Mar. 2, 2017

Related U.S. Application Data

(60) Division of application No. 14/683,152, filed on Apr. 10, 2015, now Pat. No. 9,505,815, which is a continuation-in-part of application No. PCT/CN2013/084838, filed on Oct. 8, 2013.

(30) Foreign Application Priority Data

Oct. 10, 2012 (CN) .......................... 2012 1 0383136

(51) Int. Cl.
*C07K 14/47* (2006.01)
*A61K 38/00* (2006.01)

(52) U.S. Cl.
CPC .............. *C07K 14/47* (2013.01); *A61K 38/00* (2013.01)

(58) Field of Classification Search
None
See application file for complete search history.

(56) References Cited

PUBLICATIONS

Burd et al., "Primary structures of the heterogeneous nuclear ribonucleoprotein A2, B1, and C2 proteins: a diversity of RNA binding proteins is generated by small peptide inserts", PNAS, 1989, 86(24):9788-9792.*

* cited by examiner

*Primary Examiner* — Suzanne M Noakes
(74) *Attorney, Agent, or Firm* — Matthias Scholl, PC; Matthias Scholl

(57) ABSTRACT

A cDNA, including the nucleotide sequence represented by SEQ ID NO: 2. A cDNA, including a nucleotide sequence encoding a complete protein, a protein fragment, a protein analog, or a protein derivative each including the amino acid sequence represented by SEQ ID NO: 1. A cDNA, including the nucleotide sequence encoding the amino acid sequence represented by SEQ ID NO: 1.

3 Claims, 16 Drawing Sheets

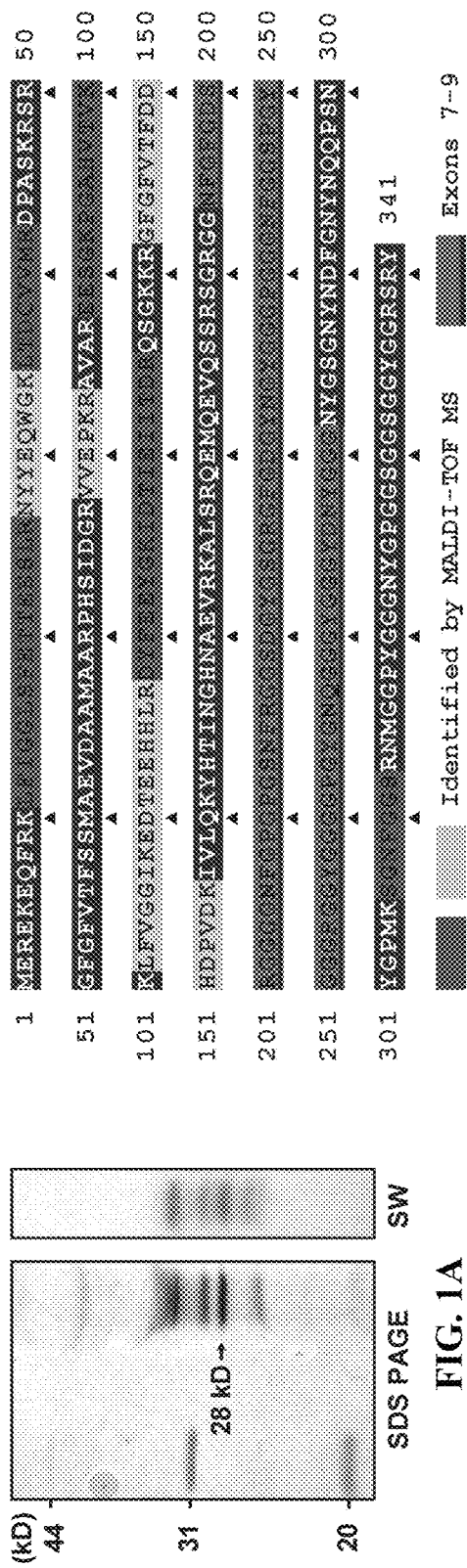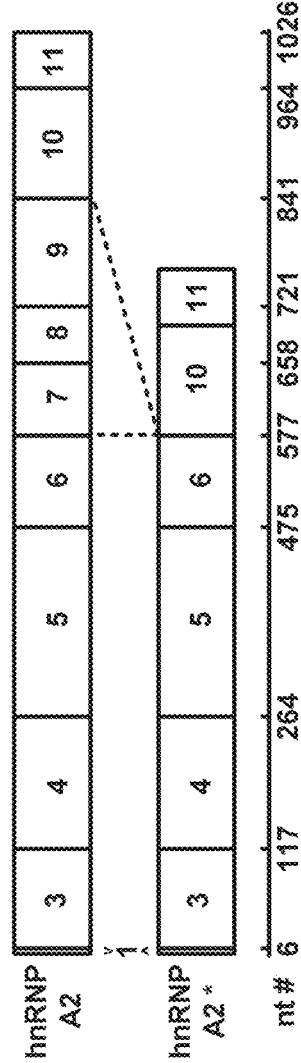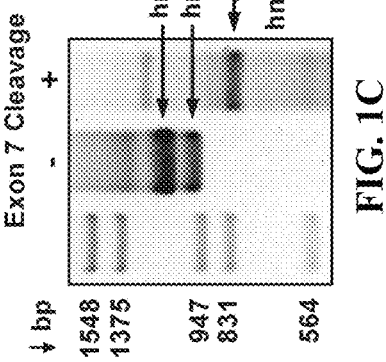

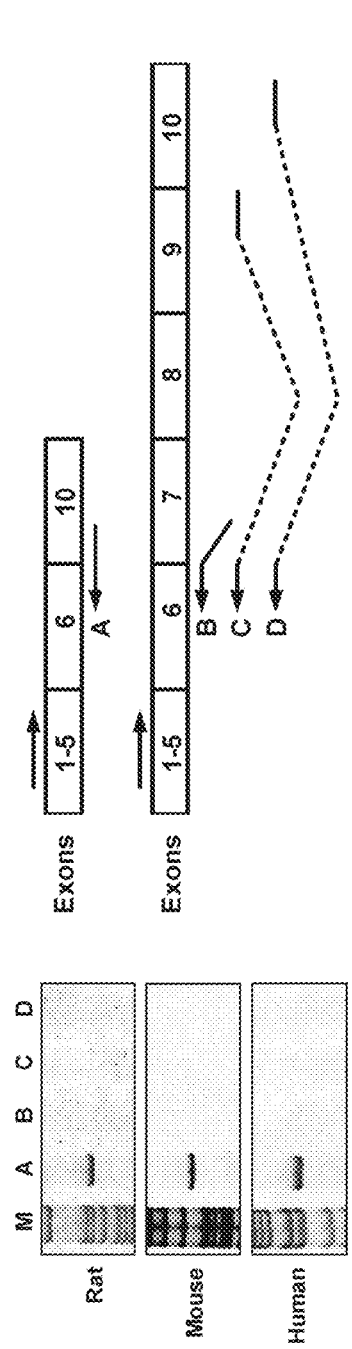
FIG. 1E
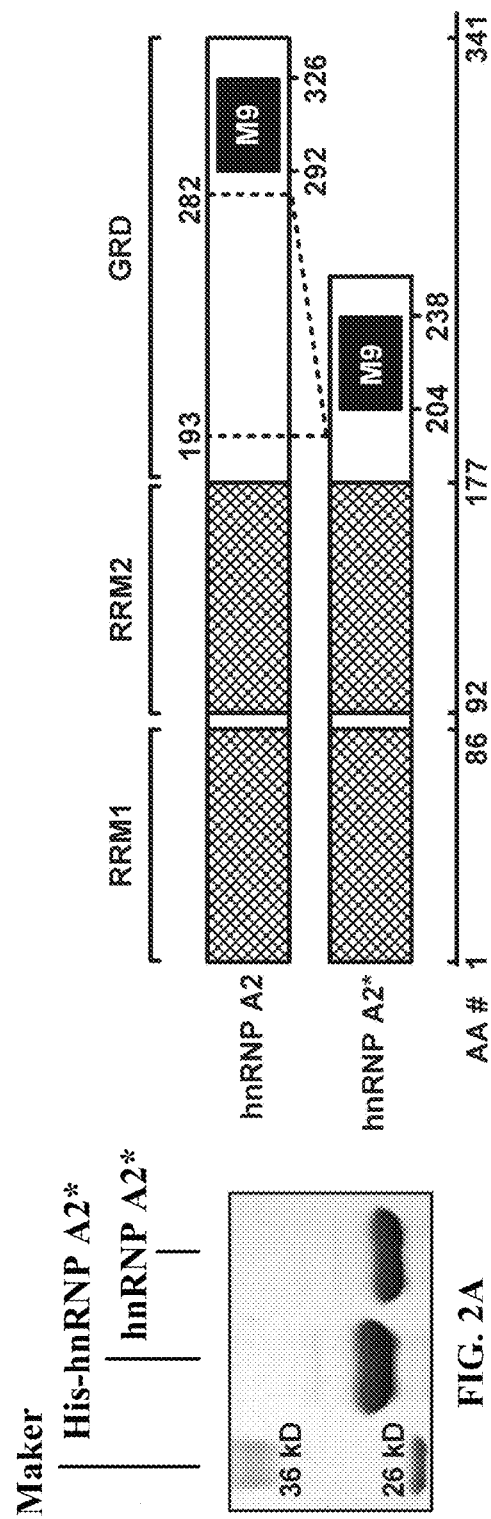
FIG. 2A
FIG. 2B

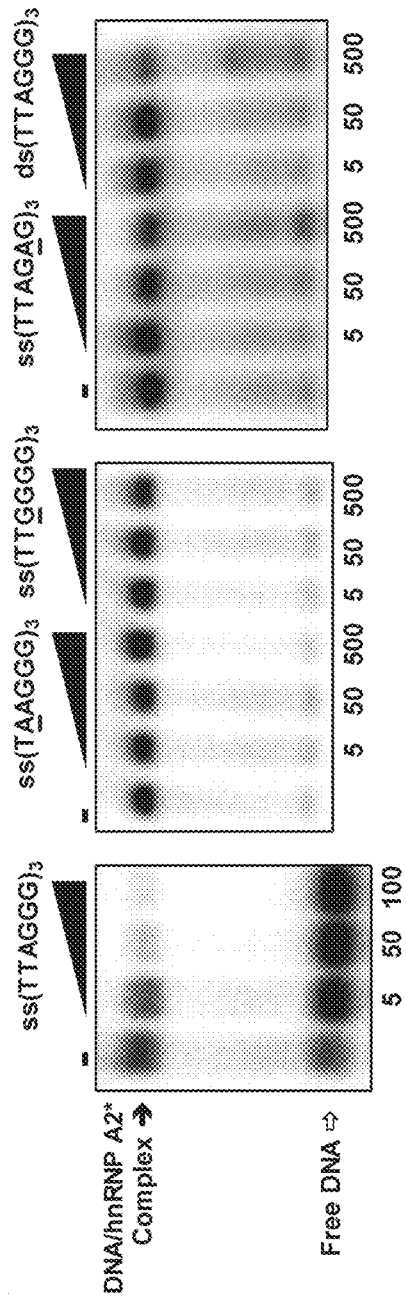
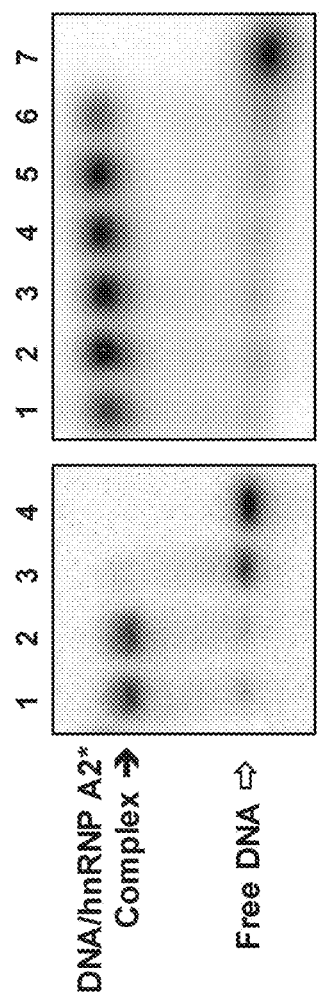
FIG. 2C
FIG. 2D
1: TTAGGGTTAGGGTTAG (SEQ ID NO:4)
2: TAGGGTTAGGGTTAG (SEQ ID NO:5)
3: AGGGTTAGGGTTAG (SEQ ID NO:6)
4: GGGTTAGGGTTAG (SEQ ID NO:7)
1: TAGGGTTAGGGTTAG (SEQ ID NO:5)
2: TAGGGTTAGGGTTA (SEQ ID NO:9)
3: TAGGGTTAGGGTT (SEQ ID NO:10)
4: TAGGGTTAGGGT (SEQ ID NO:11)
5: TAGGGTTAGGG (SEQ ID NO:12)
6: TAGGGTTAGG ← MBS (SEQ ID NO:13)
7: TAGGGTTAG

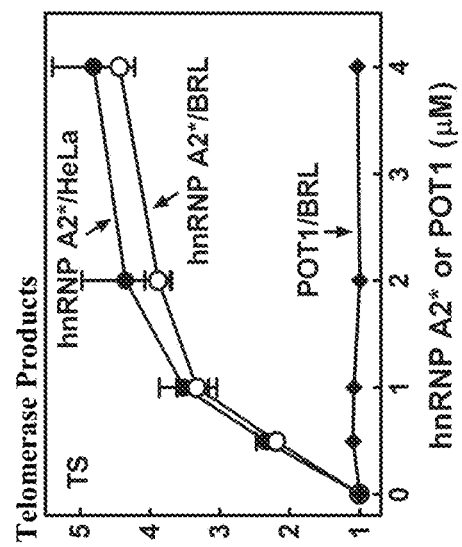
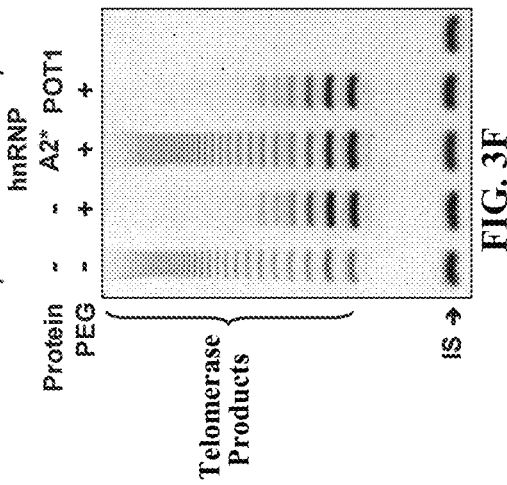
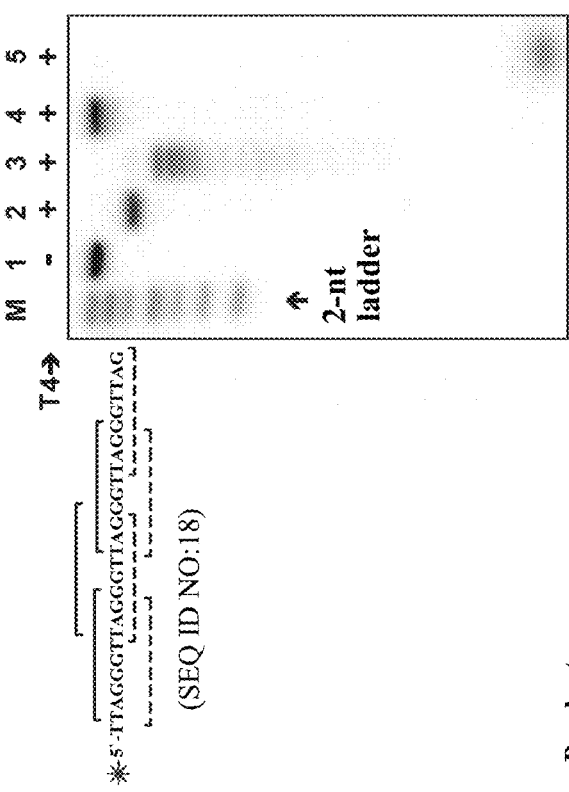
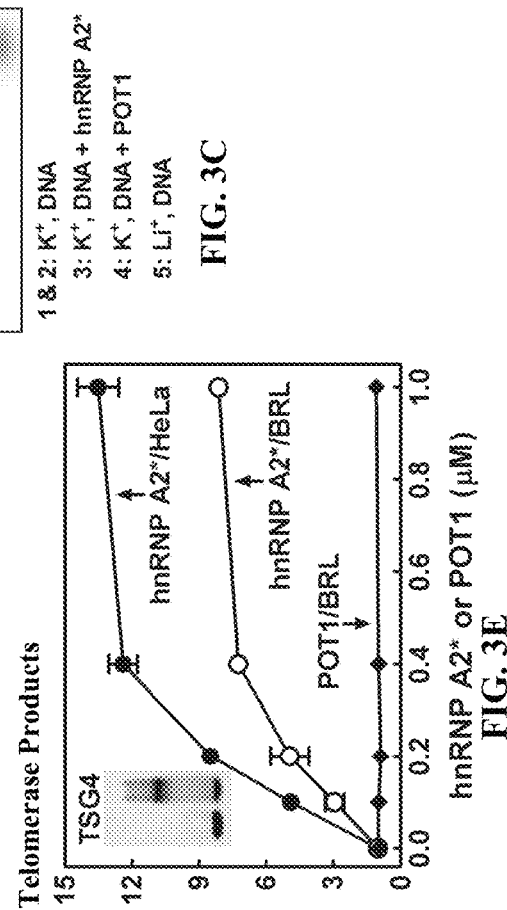

1 & 2: TTAGGGTTAGGGTTAGGGTTAG-3' (SEQ ID NO:14)
3: TTAcGGTTAGGGTTAGGGTTAG-3' (SEQ ID NO:15)
4: TTAGGGTTAGGGTTAGcGTTAG-3' (SEQ ID NO:16)
5: TTAcGGTTAGcGTTAcGGTTAG-3' (SEQ ID NO:17)

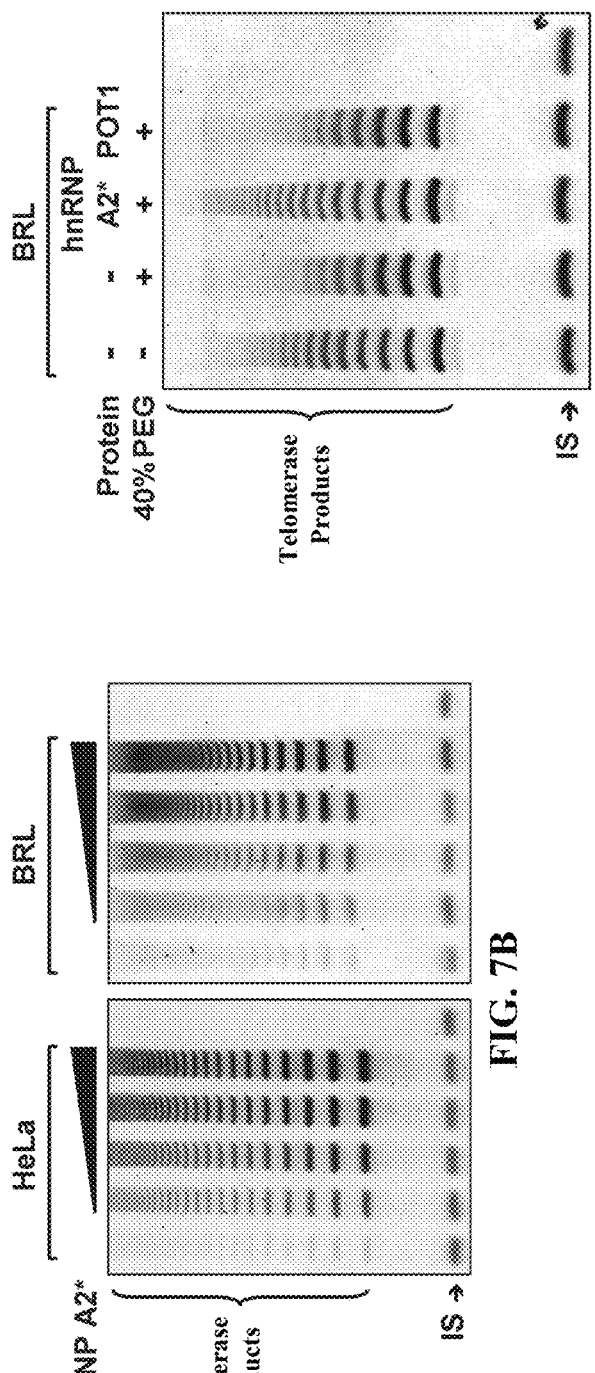
FIG. 7B
FIG. 7C
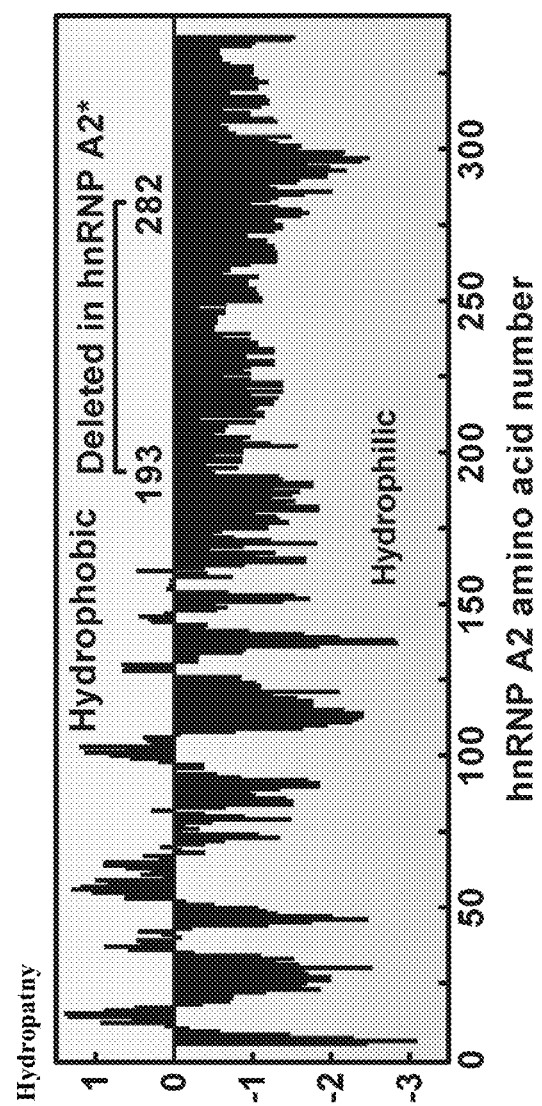
FIG. 8A

HETEROGENEOUS NUCLEAR RIBONUCLEOPROTEIN A2* (HNRNP A2*) AND NUCLEIC ACID ENCODING THE SAME

CROSS-REFERENCE TO RELATED APPLICATIONS

This application is a divisional of U.S. Ser. No. 14/683,152 filed on Apr. 10, 2015, now pending, which is a continuation-in-part of International Patent Application No. PCT/CN2013/084838 with an international filing date of Oct. 8, 2013, designating the United States, now pending, and further claims priority benefits to Chinese Patent Application No. 201210383136.6 filed Oct. 10, 2012. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to heterogeneous nuclear ribonucleoprotein A2* (hnRNP A2*), a nucleic acid encoding the protein and uses thereof.

Description of the Related Art

Human chromosome ends are protected by telomeres, which are composed of TTAGGG DNA repeats and associated proteins. Telomeres shorten with each cell division because of incomplete DNA-end replication which produces a 3' end single-stranded overhang outside the double-stranded region. Cells compensate for telomere erosion through the action of telomerase, a specialized reverse transcriptase that adds telomeric repeats to the 3' end of the telomere.

In budding yeast, the extension of telomere is mediated by Cdc13. Cdc13 is a single-stranded telomere DNA-binding protein that associates with Est1, a protein that interacts with the RNA component of yeast telomerase. Thus, Est2 (the catalytic subunit of the yeast telomerase) is recruited to the telomere according to the following route: telomere overhang→Cdc13→Est1→Tlc1→Est2. Similarly, in Tetrahymena, Teb1 bridges the interaction between telomerase and the telomere, which promotes highly processive telomere extension by telomerase. However, in mammalian cells, the telomerase is recruited to the telomere by the Cajal body, while the mechanism(s) and factors required to promote a similar interaction between the telomere and telomerase are poorly understood.

Telomere DNA can adopt a four-stranded G-quadruplex structure that can be either intermolecular and intramolecular. Although an intermolecular G-quadruplex is an excellent substrate for ciliate telomerases, an intramolecular G-quadruplex is not. In vertebrates, intramolecular G-quadruplexes (hereinafter referred to as G-quadruplex) preferentially form at the furthest 3' end of the telomeric DNA, rendering it inaccessible to telomerase. As a result, this structure inhibits telomere extension. Only a few proteins have been identified that can disrupt G-quadruplex. One such protein is protection of telomeres 1 (POT1), a component of the telomere shelterin complex that binds telomere overhangs with high affinity. When the 3' end of telomere overhang and POT1 includes a tail consisting of at least 8 nucleotides, the telomere DNA can be extended by telomerase. Given the fact that POT1 takes priority to bind the minimum binding sites (MBS) of 5'-TAGGGTTAG-3' at the 3' end, the binding of the telomere DNA by POT1 blocks telomere ends. Despite its ability to disrupt G-quadruplex, POT1 actually inhibits telomere extension by binding to the telomere end and blocking telomerase access to the overhang. Some proteins from the hnRNP family are also able to unfold telomeric G-quadruplex. These proteins interact with telomeric ssDNA and telomerase in vitro, suggesting that they play a role in telomere biology.

hnRNPs are highly abundant proteins that play important roles in RNA metabolism. For example, hnRNP A2/B 1 and A1 alone are represented by at least $10^7$ molecules per cell, whereas a typical eukaryotic cell, such as HEK-293, has 20-50 molecules of telomerase and 92 telomere ends. In principle, these proteins should saturate both telomeres and telomerase. Therefore, it is unlikely that they could play a direct role in regulating telomere extension.

SUMMARY OF THE INVENTION

In view of the above-described problems, it is one objective of the invention to provide an hnRNP A2* protein, a nucleic acid encoding the protein and uses thereof. The hnRNP A2* protein can effectively unfold the G-quadruplex structure of the telomere, significantly enhance the catalytic activity and processivity of the telomerase, extend the telomere DNA, prevent the replicative senescence of the cells, and maintain the cell division potential.

To achieve the above objective, in accordance with one embodiment of the invention, there is provided an hnRNP A2* protein, comprising an amino acid sequence represented by SEQ ID NO: 1, the protein being a complete protein, a protein fragment, a protein analogue or a protein derivative.

In a class of this embodiment, an amino acid sequence of the protein fragment, the protein analogue or the protein derivative has at least 95% similarity to the amino acid sequence represented by SEQ ID NO: 1.

In a class of this embodiment, the protein is the complete protein comprising the amino acid sequence represented by SEQ ID NO: 1.

In accordance with another embodiment of the invention, there is provided a nucleic acid comprising a nucleotide sequence encoding a complete protein, a protein fragment, a protein analogue or a protein derivative each comprising an amino acid sequence represented by SEQ ID NO: 1.

In a class of this embodiment, the nucleic acid comprises the nucleotide sequence encoding the amino acid sequence represented by SEQ ID NO: 1.

In a class of this embodiment, the nucleic acid comprises the nucleotide sequence represented by SEQ ID NO: 2.

In another aspect, the invention further provides a use of the hnRNP A2* protein, for unfolding a G-quadruplex structure of telomere thereby facilitating the telomerase-mediated telomere extension.

In a class of this embodiment, the hnRNP A2* protein can recognize the nucleotide sequence 5'-TAGGGTTAGG-3' of the telomere. The hnRNP A2* protein binds to the telomere DNA to unfold the G-quadruplex structure thereby exposing the 5'-GTTAG-3' end. The exposed 5'-GTTAG-3' end can pair the RNA template 5'-CUAAC-3' of the vertebrate telomerase so that the telomere can be extended by the catalysis of the telomerase to maintain its length.

Advantages according to embodiments of the invention are summarized as follows.

1) The invention discloses an hnRNP A2* protein extracted from mammalian cells which can interact with both the telomere and the telomerase. The hnRNP A2* protein and the telomerase can be co-located on the Cajal body and the telomere, and then actively and effectively unfold the G-quadruplex structure of the telomere. The protein binds the minimum binding site at the 3' end of the telomere and exposes a tail comprising about 5 nucleotides therein, so that the telomere can pair the RNA template of the telomerase. As a result, the catalytic activity and processivity of the telomerase are significantly improved, the telomere is extended, the telomere shortening resulting from cell division is compensated, and the cell proliferation is enhanced.

2) The invention provides technical inspiration for prolonging the life span of the cell division. The expression of the hnRNP A2* protein can alter the length of the telomere, whereby regulating the cell division ability, prolonging the life span and stimulating the proliferation of cells, and inducing the senescence of harmful cells such as cancer cells. The potential of the cell division is mainly determined by whether the shortening of the telomere DNA during the cell division can be effectively compensated. The hnRNP A2* protein can recognize the nucleotide sequence 5'-TAGGGTTAGG-3', which is one Guanylic acid more than the 3' end of the native telomere DNA. The binding of the hnRNP A2* protein and the telomere DNA can unfold the G-quadruplex structure of the telomere and expose the five nucleotides GTTAG at the endmost, thereby extending the telomere and maintain the length thereof.

3) The hnRNP A2* protein of the invention has different functions from other hnRNP family members, that is, the former can uniquely mediate the telomere extension. Moreover, the hnRNP A2* protein has low abundance and specific distributions in cells, which implies that its function is different from common hnRNP proteins. Compared with the high abundance of hnRNP, the transcript of the hnRNP A2* has an extremely low abundance, and only when the exon 7 of the hnRNP A2 and the derivatives thereof is completely sliced, can the mRNA thereof be detected using RT-PCR (as shown in FIG. 1C).

4) The hnRNP A2* protein and the nucleotide sequence encoding the protein provides diagnostic tools for diseases, such as cancer and progeria, caused by the abnormal expression of the hnRNP A2* protein. The diagnostic tools comprise hybridization with nucleic probe targeting the nucleotide sequence of the hnRNP A2* protein and antibody response targeting the hnRNP A2* protein.

BRIEF DESCRIPTION OF THE DRAWINGS

The invention is described hereinbelow with reference to the accompanying drawings, in which:

FIGS. 1A, 1B, 1C, 1D, and 1E show identification of the 28-kDa telomere-/telomerase-interacting protein hnRNP A2*. In particular, FIG. 1A shows SDS/PAGE of affinity-purified proteins (Left) and Southwestern blot (SW) probed with $^{32}$P-(TTAGG G)$_3$ (Right) (SEQ ID NO: 8). FIG. 1B shows MALDI-TOF mass spectrometric peptide mapping of the 28-kDa protein. The 28-kDa protein is a variant of hnRNP A2 protein which has the amino acid sequence represented by SEQ ID NO: 3. FIG. 1C shows PCR of hnRNP A2 and hnRNP A2* cDNA without and with the prior cleavage at exon 7 using endonuclease XhoI. The cDNAs bearing exon 7 were annealed with a cDNA at exon 7 and then cut by XhoI to prevent them from being amplified. FIG. 1D shows exons in hnRNP A2* and hnRNP A2 mRNA. FIG. 1E shows detection of hnRNP A2* mRNA in rat liver, cultured mouse (MEFs), and human HeLa cells by RT-PCR using junction primers (solid arrows).

FIGS. 2A, 2B, 2C, 2D, and 2E show binding of hnRNP A2* to telomeric DNA analyzed by EMSA. In particular, FIG. 2A shows hnRNP A2* expressed and purified from E. coli. FIG. 2B shows functional domains in hnRNP A2* in comparison with hnRNP A2. FIG. 2C shows binding of hnRNP A2* to (TTAGGG)$_3$ (SEQ ID NO: 8) in the presence of competitive DNA of increasing fold concentrations (indicated below images). FIG. 2D shows that hnRNP A2* binds a MBS of TAGGGTTAGG (SEQ ID NO: 13). Nine other different sequences of telomeric DNA are tested in comparison to MBS to confirm the MBS binding activity of hnRNP A2*. These sequences are TTAGG GTTAGGGTTAG (SEQ ID NO: 4), TAGGGTTAGGGTTAG (SEQ ID NO: 5), AGG GTTAGGGTTAG (SEQ ID NO: 6), GGGTTAGGGTTAG (SEQ ID NO: 7), TAGGG TTAGGGTTA (SEQ ID NO: 9), TAGGGTTAGGGTT (SEQ ID NO: 10), TAGGGTT AGGGT (SEQ ID NO: 11), TAGGGTTAGGG (SEQ ID NO: 12), and TAGGGTTAG (SEQ ID NO: 13). FIG. 2E shows effect of single-nucleotide mutation on the binding of hnRNP A2* to TAGGGTTAGGGTTAG (SEQ ID NO: 22). DNAs were either wild-type sequence (W) or carrying a mutation to cytosine at the position indicated above the lane. Asterisks indicate mutations that disrupt binding.

FIGS. 3A, 3B, 3C, 3D, 3E, and 3F show that hnRNP A2* actively unfolds telomere G-quadruplex, binds to the MBS at the very 3' end of telomeric DNA, exposes a 5-nt tail, and activates telomerase. In particular, FIG. 3A shows FRET analysis showing active opening of G-quadruplex by hnRNP A2* in comparison with the spontaneous opening of G-quadruplex trapped by complementary C-rich DNA. Donor fluorescence monitored in real-time upon addition of hnRNP A2* or excess C-rich DNA. FIG. 3B shows binding-site preference of hnRNP A2* to telomeric DNA that does not form G-quadruplex. The 5' $^{32}$P-labeled DNA composed of 5'-TTAGGGTTAGGGTTAGGGTT AG-3' (SEQ ID NO: 14) was incubated with hnRNP A2* before digestion with T4 polymerase (T4), which cleaves nucleotides from the 3' end. Lowercase indicates mutations introduced to manipulate the number and position of MBS (square bracket). Nucleotide sequences of these mutations are 5'-TTAcGGT-TAGGGTTAGGGTTAG-3' (SEQ ID NO: 15), 5'-TTAGGGTTAGGGTTAGcGTTAG-3' (SEQ ID NO: 16), and 5'-TTAcGGTTAGcGTTAcGGTTAG-3' (SEQ ID NO: 17). FIG. 3C shows binding-site preference of hnRNP A2* and POT1 to telomeric DNA that forms G-quadruplex. Nucleotide sequence of the telomeric DNA is 5'-TTAGGGT-TAGGGTTAGGGTTAGG GTTAG-3' (SEQ ID NO: 18). Solid square bracket indicates MBS for hnRNP A2* and dashed for POT1. G-quadruplex forms in K+ but not in Li+ solution. Other conditions are the same as those in B. FIGS. 3D and 3E show catalytic activity of telomerase from HeLa or rat cell lysate assayed by the TRAP method using nontelomeric TS (FIG. 3D) or G-quadruplex TSG4 (FIG. 3E) substrate in the presence of increasing amounts of hnRNP A2* or POT1. FIG. 3E, inset shows free TSG4 (left lane) and TSG4/hnRNP A2* complex (right lane) in EMSA. FIG. 3F shows processivity of telomerase from HeLa cell lysate assayed by the modified TRAP method using nontelomeric MTS substrate in the presence of 40% (wt/vol) PEG 200.

FIG. 4A shows TRAP assay of telomerase activity pulled down from rat cell lysate by His-hnRNP A2* immobilized on nickel beads. FIG. 4B shows binding to the RNA component of rTR of hnRNP A2* at increasing concentrations (0, 0.25, 0.5, 1 μM) examined by EMSA. FIG. 4C shows three-color immunofluorescence analysis of colocalization among hnRNP A2*, TERT, and Rap1/Coilin in cultured rat cells. RAP1 and Coilin served as markers for telomere and Cajal body, respectively. Venn diagrams at the farthest right show the number of cells and foci (in parenthesis) that were positive for each combination of markers.

FIG. 5A shows expression of hnRNP A2*, hnRNP A2, TERT, and telomerase activity in 7-wk-old rat tissues. Expression was analyzed by RT-PCR. Telomerase activity was assayed by TRAP. Relative abundance was obtained by normalizing band intensity to actin and then to brain. IS, Internal standard. FIG. 5B shows that overexpression of hnRNP A2* increases telomere length in HeLa cells. Cells were drug-selected and cultured to the indicated population doublings (PDs) after they were transfected with HA-hnRNP A2* or empty control vector. Telomere restriction fragments were detected by Southern blot (Left) and then digitized for quantification (Right). M, marker.

FIG. 6A shows changes of fluorescence intensity of G-quadruplex in fluorescence resonance transfer experiments. FIG. 6B shows changes of electrophoretic mobility after DNA G-quadruplex and free single random DNA binds to hnRNP A2* or cDNA. FIG. 6C shows that POT1 protein binds the MBS at the 3' end of telomere DNA and blocks the end. The 5' $^{32}$P-labeled DNA was incubated with POT1 before digestion with T4 polymerase (T4), which cleaves nucleotides from the 3' end. Lowercase indicates mutations introduced to manipulate the number and position of MBS (square bracket). Nucleotide sequences of these mutations are 5'-TTtGGGTTAGGGTTA G-3' (SEQ ID NO: 19), 5'-TTAGGGTTAGcGTTAG-3' (SEQ ID NO: 20), and 5'-TTtG GGTTAGcGTTAG-3' (SEQ ID NO: 21). FIG. 6D shows that telomere DNA was totally cleaved by T4 in the absence of hnRNP A2*. The first lane was a gradient reference of one nucleotide obtained by cleavage of TTAGGGTTAGGGTTAGGGTTAG (SEQ ID NO: 14) using DNaseI. Other conditions are the same as those in FIG. 3B.

FIG. 7B shows that TRAP experiments show hnRNP A2* enhances the catalytic activity of telomerase obtained from Hela cells and rat BRL cells. The experiments employed TSG4 sequence as a substrate which can form a G-quadruplex structure prior to the extension reaction. The hnRNP A2* is shown in FIG. 3E. The last lane represents the deficiency of the telomerase. FIG. 7C shows that hnRNP A2* enhances the processivity of telomerase obtained from Hela cells and rat BRL cells. The processivity detection experiment is carried out with non-telomere TS sequence as a substrate by an updated TRAP method where 40% (w/v) PEG 200 was added. The last lane represents the deficiency of the telomerase. IS lane represents the internal reference.

FIG. 8A shows the hydrophilicity of hnRNP A2. The graph includes the deletion fragment of the hnRNP A2* protein.

DETAILED DESCRIPTION OF THE EMBODIMENTS

Figure 2E:
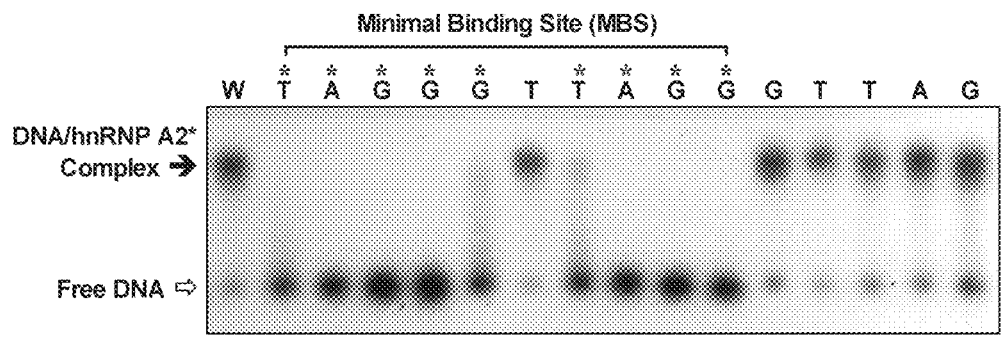

For further illustrating the invention, experiments detailing heterogeneous nuclear ribonucleoprotein A2* (hnRNP A2*), a nucleic acid encoding the protein and uses thereof are described below. It should be noted that the following examples are intended to describe and not to limit the invention.

Research ideas of the invention are illustrated by experiments to reveal the hnRNP A2* protein purification and analyze principle of G-quadruplex unfolding by hnRNP A2*, etc.

Affinity Purification of Telomeric DNA-Binding Proteins

Nuclear matrix proteins responsible for maintaining chromosome territories were isolated from rat liver (Ma H, Siegel A J, Berezney R (1999) Association of chromosome territories with the nuclear matrix. Disruption of human chromosome territories correlates with the release of a subset of nuclear matrix proteins. J Cell Biol 146:531-542).

The nuclear matrix proteins were used for affinity purification of biotin-labeled telomeric DNA oligonucleotides (TTAGGG)$_3$ conjugated to streptavidin-coated agarose beads. The purification was performed in the presence of yeast tRNA and sonicated salmon sperm DNA. Binding proteins were eluted from beads with a 2 M NaCl solution. The affinity purified proteins were resolved on 12% sodium dodecyl sulfate polyacrylamide gel electrophoresis (SDS/PAGE). A band corresponding to a 28-kDa protein was excised from gel and subjected to tryptic digestion, followed by MALDITOF mass spectrometric analysis. Data obtained were submitted to the MS-Fit Web site (http://prospector.ucsf.edu/prospector/mshome.htm) 9 segment data were returned, which indicates they matched with the segments of the hnRNPA2 protein.

hnRNP A2* cDNA Cloning and Protein Purification

DNase-treated mRNA from rat liver was reverse-transcribed into cDNA using a poly-T primer. An oligonucleotide complementary to a sequence of an exon 7 of hnRNP A2 was annealed to cDNA of hnRNP A2, and an annealed part was cleaved by an endonuclease XhoI. cDNA obtained from the reverse-transcription of mRNA of hnRNP A2* was then amplified by RT-PCR with primers 5'-TAGCTAG-CATGGAGAGAGAA AAGGAA-3' (SEQ ID NO: 23) and 5'-AAGAGCTCTCAATATCGGCTCCTTCCA-3' (SEQ ID NO: 24) using exon removal method (Wang F, Zhao Y, Hao Y H, Tan Z (2008) Identification of low-abundance alternatively spliced mRNA variants by exon exclusive reverse transcriptase polymerase chain reaction. Anal Biochem 383: 307-310). The amplicon was cloned into the NheI/SacI site of pET-28b, and an obtained plasmid is transformed into the *E. coli* strain BL21 (DE3) (provided by Beijing Bioteke Biotechnology Co. Ltd). Transformed cells were cultured in an LB medium at 37° C. for 4 hrs. 1 mM of isopropyl-β-D-thiogalactoside was used to induce protein expression of hnRNP A2* with a His$_6$ tag. After 2 hrs induction, *E. coli* cells were harvested and lysed by sonication in one pellet volume of a buffer A [50 mM NaH$_2$PO$_4$ (pH 8.0), 300 mM NaCl, 40 mM imidazole, 1 mM dithiothreitol (DTT), and 1 mM phenylmethylsulfonyl fluoride] at 4° C. A resulting cell lysate was centrifuged in the presence of a 20000×g at 4° C. for 20 min, and an obtained supernatant was loaded on an affinity HisTrap HP column. After washing with the buffer A for 10-column volume, the His-hnRNP A2* was eluted from the column with a buffer B [50 mM NaH$_2$PO$_4$ (pH 8.0), 300 mM NaCl, and 40 mM imidazole].

Preparation of Rat Telomerase RNA (rTR) Sequence

The rTR sequence was performed with reverse transcription polymerase chain reaction (RT-PCR) amplification and cloned into a pMD19-T plasmid. Restriction enzyme cleavage sites existing in the rTR sequence were cleaved by restriction endonucleases Crf 131, Rsa I, FspB I, and BamH I. The plasmid was linearized. The linearized plasmid was performed with transcription with a T7 transcription kit, and a transcript product was labeled with [γ-$^{32}$P] ATP in the presence of a T4 polynucleotide kinase.

Electrophoretic Mobility Shift Assay (EMSA)

80 nM oligonucleotides having 5' ends labeled with [γ-$^{32}$P] ATP ($^{32}$P-labeled oligonucleotides) were incubated with 400 nM recombinant hnRNP A2* at 4° C. for 30 min in a binding buffer [10 mM Tris(hydroxymethyl)methyl aminomethane (Tris) (pH 8.0), 1 mM ethylenediaminetetraacetic acid (EDTA), and 150 mM KCl] and resolved on a 8% (wt/vol) native PAGE gel. The gel was then visualized by phosphoimaging using a Typhoon PhosphorImager.

T4 Polymerase Hydrolysis Assay 50 nM $^{32}$P-labeled oligonucleotides were incubated with 1.5 μM hnRNP A2* or POT1 at 4° C. for 15 min in the binding buffer [10 mM Tris (pH 8.0), 1 mM EDTA, and 150 mM KCl], then incubated at 4° C. for 1 min after being added with 0.5 U of T4 polymerase and 1 μL 10×endonuclease buffer [330 mM Tris-acetate (pH 7.8), 100 mM Mg(CH$_3$CO$_2$)$_2$, and 5 mM DTT] for carrying out cleavage. The reaction was stopped by phenol-chloroform extraction, followed by ethanol precipitation. The products were resolved on a 19% (wt/vol) polyacrylamide gel containing 7 M urea.

Preparation of Telomerase Extract

HeLa cells or rat RRL-3A cells extract was prepared as described (Kim N W, Piatyszek M A, Prowse K R, Harley C B, West M D, et al. (1994) Specific association of human telomerase activity with immortal cells and cancer. Science 266:2011-2015). The cell extract was performed with affinity purification using (TTAGGG)$_3$ having the 5' end labeled with a biotin conjugated to a streptavidin-agarose to remove guanine-rich telomeric DNA sequence binding protein.

Analysis of Telomerase Catalytic Activity

The analysis of catalytic activity of telomerase was carried out with telomeric repeat amplification protocol (TRAP) using either TS (5'-AATCCGTCGAGCAGAGTT-3') (SEQ ID NO: 25) or TSG4 (5'-GGGCTAGGGCTAGGGCTAGGGAGTT-3') (SEQ ID NO: 26) as substrates. The telomerase substrates were incubated in the presence of different concentrations of hnRNP A2* or POT1 the telomerase extract from 5,000 cells in 50 μL volume. After being added with 0.25 mM dNTP, extension reaction was carried out at 30° C. (TS) or 37° C. (TSG4) for 10 min and stopped by heating the sample to 75° C. for 5 min Phenol-chloroform extraction and ethanol precipitation were conducted in the presence of internal reference standard sequences (5'-AATCCGTCGAGCAGAGTTAAA AGGCCGAGAAGCGAT-3' (SEQ ID NO: 27) and 5'-ATCGCTTCTCGGCCTTTT-3' (SEQ ID NO: 28) were used for TS substrate, and 5'-GGGCTAGGGCTAGGGCTAGGG AGTTAAGCGGC-CGAGAAGCGAG-3' (SEQ ID NO: 29) and 5'-CTCGCT-TCTCGGC CGCTT-3' (SEQ ID NO: 30) were used for TSG4 substrate). Obtained products were amplified by PCR (33 cycles: 94° C. for 30 s; 59° C. for 30 s), in which TS and 5'-GCGCG GCTTACCCTTACCCTTACCCTAACC-3' (SEQ ID NO: 31) were used as primers to amplify the TS substrate, and TSG4 and 5'-GTGCCCTTACCCTTACCCT-TACCCTAA-3' (SEQ ID NO: 32) were used as primers to amplify the TSG4 substrate. The PCR products were resolved on a 12% native polyacrylamide gel, stained with ethidium bromide, and visualized on a ChemiImager 5500. Telomerase activity was represented by a multiple of that of the control group of hnRNP A2* or POT1 based on the equation (TP/TPOx(ISO/IS) where TPO and ISO represent a total amount of a telomerase catalytic product and a total amount of an internal reference product, respectively, and TP and IS represent total amounts of the product obtained in the presence of hnRNP A2* and POT1, respectively.

Analysis of Telomerase Processivity

A modified version of TRAP assay as described (Xue Y, Kan Z Y, Wang Q, Yao Y, Liu J, et al. (2007) Human telomeric DNA forms parallel-stranded intramolecular G-quadruplex in K+ solution under molecular crowding condition. J Am Chem Soc 129: 11185-11191) was conducted using TSNT as the internal reference to analyze telomerase processivity. MTS substrate was incubated in a 50 μL volume containing a telomerase extract from 5,000 cells, 0.25 mM dNTP, and 0.5 μM hnRNP A2* or POT1 in the presence or absence of 40% PEG-200 for 10 min, and the reaction was stopped by heating the sample to 75° C. for 5 min. Thereafter, phenol-chloroform extraction and ethanol precipitation were conducted after added with internal reference sequences (5'-AGCATCCGTCGAGCAGAGT-TAAAAGGCCGAGAAGCGAT-3' (SEQ ID NO: 33) and 5'-ATCGCTTCTCGGCCTTTT-3') (SEQ ID NO: 28). Obtained oligonucleotides were amplified by PCR (2 cycles: 94° C. for 30 s, 55° C. for 60 s, and 72° C. for 90 s; and 29 cycles: 94° C. for 30 s, 63° C. for 30 s, and 72° C. for 30 s) in the presence of 10 pmol RP, 0.02 pmol RPC3 g, and 1 U Taq DNA polymerase. The PCR products were resolved on the 12% native polyacrylamide gel, stained with ethidium bromide, and visualized on a ChemiImager 5500.

Preparation of Subcellular Fractions and Western Blot

Subcellular fractions were acquired as described (Luderus M E, van Steensel B, Chong L, Sibon O C, Cremers F F, et al. (1996) Structure, subnuclear distribution, and nuclear matrix association of the mammalian telomeric complex. J Cell Biol 135: 867-881) with minor modification. Briefly, hnRNP A2* transfected BRL-3A cells was washed twice by a cold Earle's solution and suspended in a 10 times volume of RSB solution [0.1 M NaCl, 1.5 mM magnesium chloride, 10 mM Tris-HCl (pH 7.4), and 0.1% digitonin] at 4° C. for 10 min The cells were lysed by passing through a 19.5-gauge needle five times. The cell lysate was centrifuged at 23000×g for 30 min in a RSB solution containing 10% glycerine. A supernatant from the centrifuge was collected as a cytoplasmic extract. Nuclei collected from a precipitation was incubated in the RSB solution at 37° C. for 20 min and lysed with an LIS solution [10 mM LIS, 100 mM lithium acetate (LiAc), 1 mM EDTA, 0.1% digitonin, 0.05 mM spermine, 0.125 mM spermidine, 0.25 mM PMSF, and 20 mM Hepes-KOH (pH 7.4)] at the room temperature for 20 min with $2\times10^6$ cells per milliliter the LIS solution. LIS-treated nuclei were then centrifuged at 20000×g for 20 min, and a supernatant and a pellet were collected as a nucleoplasmic and nuclear matrix fraction, respectively. Proteins of the three cell ingredients were resolved on the 10% SDS/PAGE and transferred to a nitrocellulose membrane. HA-hnRNP A2* and hnRNPA2/B 1 were detected by mouse anti-HA monoclonal antibody and goat anti-hnRNP A2/B 1 polyclonal antibody, respectively.

Telomerase Activity and mRNA Levels in Different Rat Tissues

Organs were taken immediately after male rats were killed for analyzing telomerase activity and extracting RNA. For telomerase activity assay, tissues to be tested were added with the lysate with 0.5 miligram tissues per milimiter telomerase extract lysate, homogenized with a sterile Duall tissue grinder, and incubated for 30 min on ice. Cell lysate was centrifuged at 12000×g for 30 min at 4° C. The resulting supernatants were frozen in liquid nitrogen, and stored at −80° C. until use. Protein concentration of the supernatants was determined using Bradford assay. Total protein (200 ng) was used in each TRAP assay. An amount of RNA was detected by RT-PCR. 0.05 μg of total RNA was conducted with reverse transcription with MMLV reverse transcriptase and PCR amplification.

Cell Culture

BRL-3A rat and HeLa cells were cultured at 37° C. under 5% $CO_2$ in DMEM medium supplemented with 10% FBS, penicillin (100 units/mL), and streptomycin (0.1 mg/mL).

Retroviral Vectors and Virus Production hnRNP A2* cDNA was amplified by PCR with HM6 forward primer 5'-GATGGT ACCATGGAGAGA-GAAAAGGAACAGTTC-3' (SEQ ID NO: 34) and HM6 antisense primer 5'-GACGAATTCATTCTCAATATCG-GCTCCTTCCAC-3' (SEQ ID NO: 35), and the amplified fragment was inserted into the KpnI/EcoRI sites of the pHM6 expression vector. The HA-hnRNP A2* segment was then amplified by the T7 promoter forward primer 5'-TAATACGAGTCACTATAGGGA-3' (SEQ ID NO: 36) and the HM6 antisense primer and was cloned into the pGEM-T vector. HA-hnRNP A2* could then be subcloned into the NotI-EcoRI sites of pQCXIN retroviral vector (for BRL-3A cells) or EcoRV-KpnI sites of pMSCV-IThy1-1 retroviral vector (for HeLa cells). The recombinant pGEM-T HA-hnRNP A2* vector was transfected into EcoPack 2-293 cells and pMSCVIThy1-1 HA-hnRNP A2* was transfected together with pGagpol and pMD.G-VSVG-env into 293T cells to produce retrovirus. Medium containing the virus was collected 48 h after the transfection.

Stable Expression of HA-hnRNP A2* in Rat BRL-3A

Rat BRL-3A at about 70% confluence were exposed to a mixture of a virus-containing medium and a fresh culture medium with a ratio of 1:1 for 12 h. The culture medium for BRL-3A cells was then replaced by a fresh medium containing 800 μg/mL G418, and the culture medium for HeLa cells was then replaced by a fresh medium containing 300 μg/mL G418. BRL-3A cells were cultivated in the new medium for two weeks, and the HeLa cells were cultivated in the concentration of 100 μg/mL G418. The BRL-3A cells were cloned cells whereas the HeLa cells were non-cloned cells.

Immunofluorescence Microscopy

BRL-3A cells growing on coverslips with were fixed for 8 min at the room temperature in a PBS (pH 7.4) containing 2% paraformaldehyde and permeabilized in a PBS buffer containing 0.5% Triton X-100 in PBS. The BRL-3A cells on the coverslips were then blocked with 10% serum from the same species as the secondary antibody. Primary antibodies used included goat or rabbit polyclonal anti-TERT, rabbit polyclonal anti-Coilin, mouse monoclonal anti-HA, rabbit polyclonal anti-hRAP1. Secondary antibodies included Cy3-conjugated donkey anti-goat, fluorescein-conjugated goat or donkey anti-mouse, and DyLight649-conjugated donkey anti-rabbit at the dilutions recommended by the manufacturers. The incubation time was 1 h for the primary antibody and 45 min for the secondary antibody at the room temperature, followed by PBS washes (four times; 5 min each). Coverslips were mounted with VECTASHIELD mounting medium containing 0.5 μg/mL DAPI. Images were acquired with a Zeiss 510 META confocal microscope using a 100×oil objective.

Preparation of POT1

Recombinant human POT1 protein was prepared as described (Kelleher C, Kurth I, Lingner J (2005) Human protection of telomeres 1 (POT1) is a negative regulator of telomerase activity in vitro. Mol Cell Biol 25:808-818.). The plasmid pET-14-POT1 (gift from Joachim Lingner, Swiss Institute for Experimental Cancer Research, Lausanne, Switzerland) was transformed into the E. coli strain BL21 (DE3). The cells were grown in a TB medium supplemented with 1% glucose and 0.05 mg/mL carbenicillin at 37° C. for 5 h. POT1 expression was induced with 5 μM isopropyl thiogalactoside for an additional 2 h at 25° C. Cells were harvested and suspended in one pellet volume of a buffer C [20 mM $NaH_2PO_4$ (pH 8.0), 200 mM NaCl, 0.2% Tween-20, 10 mM imidazole, 20% glycerol, and 5 mM β-mercaptoethanol] containing 1 mg/mL of lysozyme. Cells were allowed to stand at 4° C. for 20 min and sonicated. A lysate was centrifuged at 20,000×g for 20 min at 4° C., and a supernatant was loaded on the affinity HisTrap HP column. After washing with the buffer A for 10-column volume, the His-POT1 was eluted from the column with the buffer C containing 400 mM imidazole. Purified proteins were dialyzed against a buffer D [20 mM NaH$_2$PO$_4$ (pH 8.0), 50 mM NaCl, 0.2% Tween-20, 20% glycerol, and 5 mM β-mercaptoethanol] and stored at −70° C.

Analysis of G-Quadruplex Unfolding by hnRNP A2*

Oligonucleotide GGG(TTAGGG)$_3$ (SEQ ID NO: 37) labeled with a fluorescein (FAM) (donor) at the 5′ end and a tetramethylrhodamine (TMR) (acceptor) at the 3′ end was mixed with 200 nM hnRNP A2* or 1 μM cDNA CCC (TAACCC)$_3$ (SEQ ID NO: 38) in a Tris-EDTA (TE) buffer (pH 8.0) containing 150 mM KCl. The kinetics of G-quadruplex opening upon addition of hnRNP A2* or cDNA was immediately monitored at 25° C. by recording the donor fluorescence at 515 nm using a slit of 5 nm and an excitation wavelength of 480 nm PCR Amplification of hnRNP A2* in Rat, Mouse, and Human Cells PCR was conducted in 25 μL volume with cDNA transcribed using a poly(T) primer from 0.2 μg of RNA of rat BRL-3A cells, HeLa cells, and mouse liver, respectively. Amplification was carried out with an initial denaturation at 94° C. for 2 min, followed by 32 cycles for human and mouse samples (29 cycles for rat samples) of 94° C. for 30 s, 62° C. for 30 s, and 72° C. for 30 s.

Telomerase Pull-Down by hnRNP A2*

Telomerase pull-down was conducted as described (Eversole A, Maizels N (2000) In vitro properties of the conserved mammalian protein hnRNP D suggest a role in telomere maintenance. Mol Cell Biol 20:5425-5432.) with minor modifications. BRL-3A cells (1×10$^6$) were lysed in 100 μL of a CHAPS buffer [0.5% CHAPS, 10 mM Tris (pH 8.0), 1 mM MgCl2, and 0.1 mM PMSF]. A total of 30 μg of recombinant His-tagged hnRNP A2* was immobilized to a nickel resin. The beads were blocked with 1% BSA at 4° C., followed by two washes with a cold CHAPS buffer, and 100 μL of cell lysate and 100 μL of the CHAPS buffer were added and incubated at 4° C. for 2 h. After three times washing with the cold CHAPS buffer, the beads were used to detect telomerase activity using the TRAP method. Untreated beads or cell extract pretreated with 200 μg/mL RNase A for 30 min were used as controls.

Telomeric Restriction Fragment Measurement

The average length of telomeric restriction fragment (TRF) was measured as described (Zhao Y, Sfeir A J, Zou Y, Buseman C M, Chow T T, et al. (2009) Telomere extension occurs at most chromosome ends and is uncoupled from fill-in in human cancer cells. Cell 138:463-475.).

siRNA Knockdown of TERT in Rat Cells

A short interfering (si) RNA duplex targeting rat TERT sequence (GCCAGCATG TTAGGAAGAA) (SEQ ID NO: 39) was provided by RiboBio Co., Ltd (Guangzhou, China). Nontargeting siRNA was used as a control. Cells growing on a coverslip of a 6-well cell culture plate were incubated with 50 nM siRNA in 2 mL of medium containing Lipofectamine 2000. Cells were then examined for the expression of TERT protein using immunofluorescence microscope. A primary antibody TERT (D-16) utilized was provided by Santa Cruz Co., Ltd. An FITC-labeled donkey anti-goat secondary antibody was provided by Protein Tech Group, Inc.

Results

Identification of hnRNP A2*, a Single-Stranded Telomeric DNA-Binding Protein from the Nuclear Matrix.

The nuclear matrix was prepared, and the single-stranded telomeric DNA-binding protein was isolated by affinity purification and then resolved on the SDS/PAGE (FIG. 1A, Left). Binding activities of the telomere-binding proteins was identified by Southwestern blot using the $^{32}$P-labeled (TTAGGG)$_3$ probe (FIG. 1A, Right). The most abundant protein, with a molecular mass of 28 kDa, was excised from the gel and analyzed by MALDI-TOF mass spectrometry (Table 1). Nine of the tryptic peptides from this protein mapped to hnRNP A2, with eight peptides being found within the N-terminal half and one near the C terminus (FIG. 1B). Because the peptides span a region of hnRNP A2 greater than 28 kDa, it was speculated that the newly isolated telomere-binding protein is a splice variant of hnRNP A2 (36 kD) lacking these exons. To test this, a newly developed "exon-exclusive RT-PCR" (Wang F, Zhao Y, Hao Y H, Tan Z (2008) Identification of low-abundance alternatively spliced mRNA variants by exon exclusive reverse transcriptase polymerase chain reaction. Anal Biochem 383: 307-310) was used to specifically amplify the variant (FIG. 1C). Sequence analysis of the PCR product confirmed it is an hnRNP A2 isoform lacking exons 7-9 (FIG. 1D). hnRNP A2* is a conserved protein that is expressed in rat, mouse, and human cells (FIG. 1E).

TABLE 1

MALDI-TOF mass spectrometry of hnRNP A2*

| m/z submitted | MH+ matched | Delta Da | start | end | Peptide Sequence | SEQ ID NO: | Modifications |
|---|---|---|---|---|---|---|---|
| 727.3752 | 727.4466 | −0.0714 | 78 | 83 | (R)VVEPKR(A) | 40 | |
| 781.4059 | 781.3593 | 0.0466 | 298 | 305 | (K)SGNEGGSR(N) | 41 | |
| 1087.4952 | 1087.4849 | 0.0103 | 27 | 34 | (R)NYYEQWGK(L) | 42 | |
| 1087.4952 | 1087.4681 | 0.0271 | 35 | 42 | (K)LTDCVVMR(D) | 43 | 1PO4 1Cys-am |
| 1188.6464 | 1188.6476 | −0.0012 | 126 | 135 | (K)IDT1EIITDR(Q) | 44 | |
| 1338.6715 | 1338.7018 | −0.0302 | 88 | 100 | (R)EESGKPGAHVTVK(K) | 45 | |
| 1695.7682 | 1695.7655 | 0.0028 | 142 | 156 | (R)GFGFVTFDDHDPVDK(I) | 46 | |
| 1798.9305 | 1798.9227 | 0.0077 | 11 | 26 | (K)LFIGGLSFETTEESLR(N) | 47 | |
| 1879.9572 | 1879.9666 | −0.0094 | 102 | 117 | (K)LFVGGIKEDTEEHHLR(D) | 48 | |
| 2220.0923 | 2220.0712 | 0.0211 | 118 | 135 | (R)DYFEEYGKIDTIEIITDR(Q) | 49 | | hnRNP A2* Uniquely Binds Single-Stranded Telomeric TTAGGG Repeats.

The cDNA encoding hnRNP A2* was cloned and expressed in *Escherichia coli*, producing a recombinant protein with the expected molecular mass (FIG. 2A). The exons 7-9 coded the glycine-rich domain (GRD) and provided additional DNA/RNA binding sites in addition to two RNA recognition sites (RRM). The EMSA result revealed that the deletion of exons 7-9 of hnRNP A2* leads the high binding specificity to the Telomeric DNA and that hnRNP A2* binds the ssDNA telomeric repeat (TTAGGG)$_3$ with high specificity but has very low or no binding affinity for (TAAGGG)$_3$, (TTGGGG)$_3$, (TTA GAG)$_3$, or double-stranded (TTAGGG)$_3$ (FIG. 2C). This is in contrast to hnRNP which has a broad DNA-binding specificity with the consensus sequence N(A,C,T)(C,T)(A,G) G(C,G,T)(A,T) NNN. Results of additional EMSA experiments using different sizes of telomeric DNA revealed a minimal binding site (MBS) of 5'-TAGGGTTAGG-3' (SEQ ID NO: 13) for hnRNP A2* (FIG. 2D), and this sequence resembles the MBS of human POT1 except that it is 1 nt longer at the 3' end. The binding specificity of hnRNP A2* was further verified by constructing 10 mutant variants of the MBS, each carrying a single mutation to cytosine at each nucleotide. All the mutations within the MBS abolished the bindings except the mutations of thymines in the vicinity of GGG (FIG. 2E). These results further demonstrated the exquisite binding specificity of hnRNP A2*. Mutations outside of the MBS did not affect binding.

hnRNP A2* Actively Unfolds G-Quadruplex, Preferentially Binds to the MBS at the 3' End of Telomeric DNA, and Exposes a Five-Nucleotide 3' Tail.

Figure 3A:
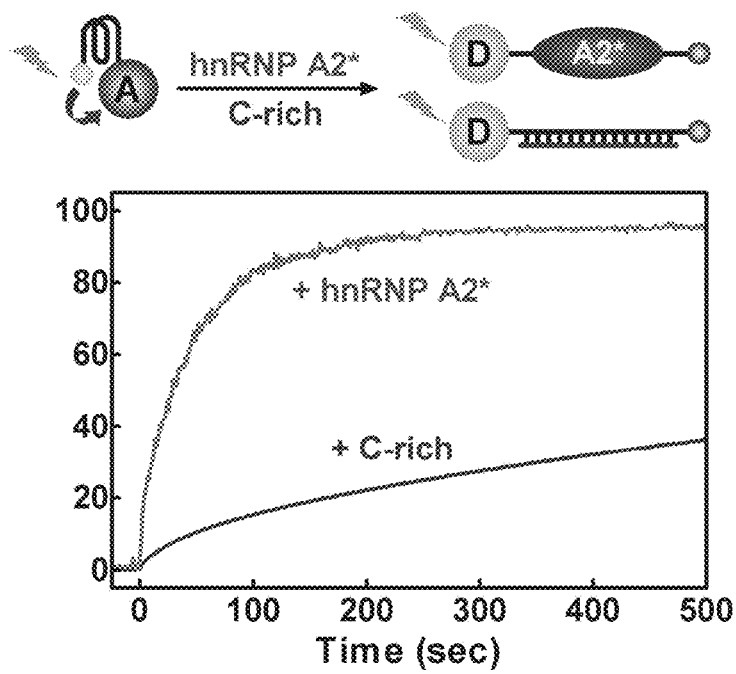
Figure 6A:
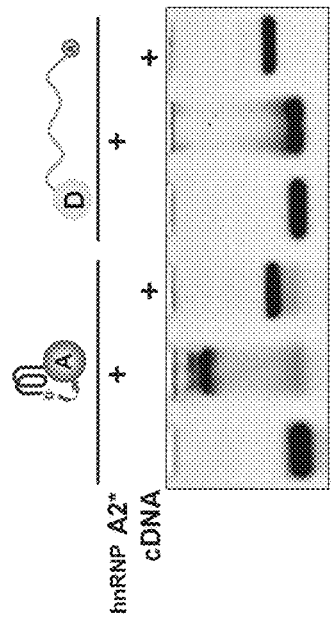
FIGS. 6A, 6B, 6C, and 6D show that hnRNP A2* uniquely unfolds telomere G-quadruplex. In particular.
Figure 6B:
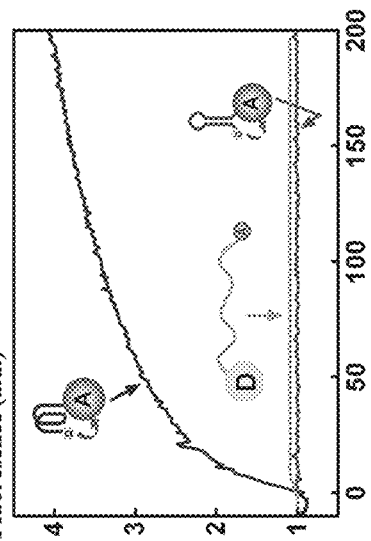

The interaction between hnRNP A2* and telomeric G-quadruplex was analyzed using fluorescence resonance energy transfer (FRET). 5'-(GGGTTA)$_3$GGG-3' was labeled with fluorescein (FAM) at the 5' end (the FRET donor) and tetramethylrhodamine (TAMRA) at the 3' end (the FRET receptor) (FIG. 3A). When this oligomer forms G-quadruplex, the two fluorophores are closely juxtaposed and FRET occurs between the two fluorophores, suppressing the donor fluorescence. When G-quadruplex was incubated with hnRNP A2*, donor fluorescence increased rapidly, suggesting that hnRNP A2* promotes G-quadruplex unwinding, which separates the two from each other and weakens the energy transfer from the FRET donor to the FRET receptor. It was noted that the rate of fluorescence increase and G-quadruplex unwinding in the presence of hnRNP A2* was much faster than the slow spontaneous unwinding of G-quadruplex in the presence of excess complementary 5'-CCC (ATTCCC)$_3$-3', which suggests that hnRNP A2* actively unfolds G-quadruplex, whereas the FRET was not altered by hnRNP A2* when an irrelevant linear and hairpin DNA substrate was used (FIGS. 6A-6B).

Figure 3B:
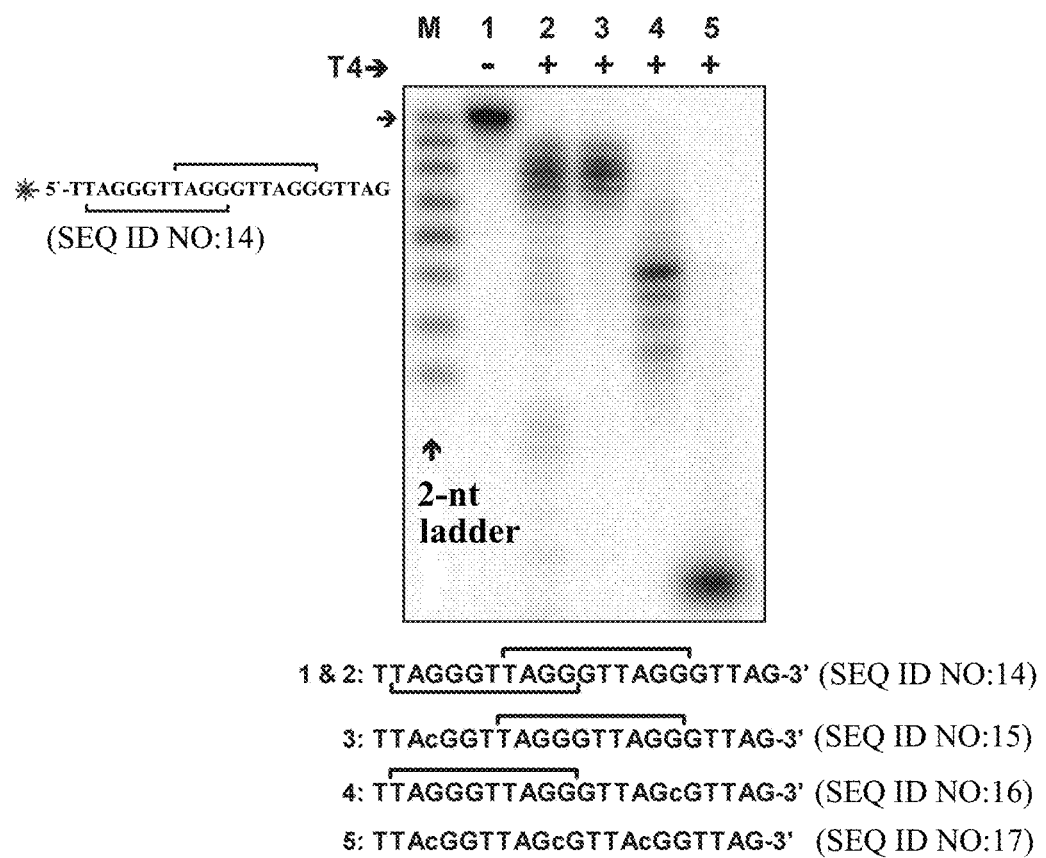
Figure 6C:
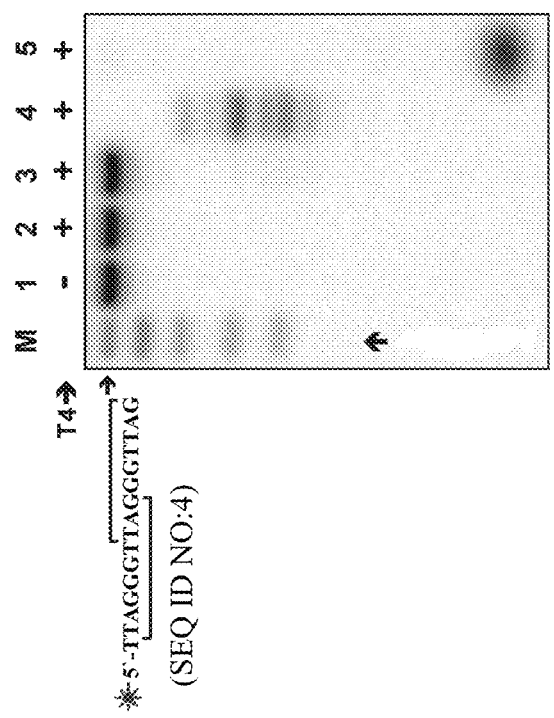
Figure 6D:
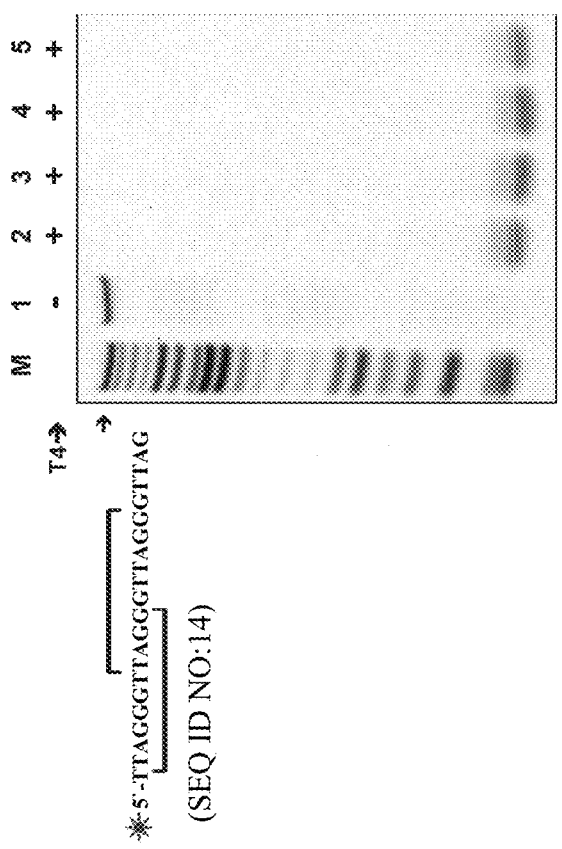

The 3'-terminal sequence of most native telomeres is TTAG-3'. To compare the binding ability of hnRNP A2* and POT1 to the 3' end, linear telomeric DNA was digested by T4 DNA polymerase in the presence of hnRNP A2* or POT1. The results show that both hnRNP A2* and POT1 bind to their respective MBS at the very 3' end when more than one MBS was available, and thus the exposed tail of hnRNP A2* is GTTAG-3' (FIG. 3B), and POT1 protected the entire DNA substrate from cleavage (FIG. 6C) Importantly, the same 3'-end preference and specificity for each protein was observed when the DNA substrate was telomeric G-quadruplex (FIG. 3C). These results do not reflect secondary structure in the DNA substrate, because they were completely susceptible to digestion by T4 DNA polymerase in the absence of protein (FIG. 6D).

hnRNP A2* Enhances the Catalytic Activity and Processivity of Telomerase In Vitro.

Figure 7A:
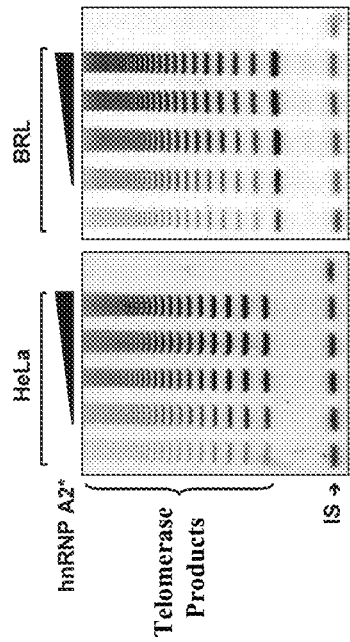
FIG. 7A shows hnRNP A2* enhances the catalytic activity of telomerase of Hela cells and rat BRL cells. TRAP experiments employ non-telomere TS sequence to detect telomerase activity. The hnRNP A2* is shown in 3D. The last lane represents the deficiency of the telomerase.

The exposed tail 5'-GTTAG-3' of hnRNP A2* is complementary to and forms Watson-Crick base pairs with 5'-CUAAC-3' in the RNA template of vertebrate telomerase. It is, thus, conceivable that the binding of hnRNP A2* and the tail of the telomere could enhance the telomerase activity. This possibility had been tested in vitro using a conventional TRAP, and hnRNP A2* significantly enhanced the activity of human or rat telomerase (rTR) (FIGS. 3D, 7A). Because the TRAP assay uses a nontelomeric TS substrate, telomerase must synthesize several telomeric repeats before hnRNP A2* binds and/or G-quadruplex can form. The results suggest that hnRNP A2* may stimulate telomere extension by inhibiting formation of G-quadruplex and leaving an appropriate 3'-terminal sequence available for telomerase binding. In contrast, POT1 does not stimulate telomerase in a TRAP assay. This result is consistent with a previous study, which reported that POT1 did not stimulate telomerase activity, by a direct, non-PCR-based method using a nontelomeric primer. These data support the proposal that "POT1 may modulate telomerase activity by regulating the access of telomerase to the primer but not during extension".

The ability of hnRNP A2* to unwind telomeric G-quadruplex was also examined by a modified TRAP assay using TSG4 as a substrate in which a thymidine next to the G-tract was mutated into cytosine so that it forms G-quadruplex but is still recognized by hnRNP A2* (FIG. 2E). Such mutation enables the TSG4 substrate to differ from the extended sequence region, so that PCR amplification can be realized. It was founded from experiments that hnRNP A2* stimulates the telomerase activity to the TSG4 to a greater extent (FIGS. 3E, 7B) compared with the nontelomeric TS substrate (FIGS. 3D, 7A), which indicates that hnRNP A2* promotes telomerase function by unfolding G-quadruplex during telomerase extension. In the contrary, POT1 does not stimulate telomerase activity with either DNA substrate (FIG. 3E).

Although human telomerase can processively add multiple telomeric repeats to a single primer, processive DNA synthesis by telomerase is inhibited by G-quadruplex, because it interferes with telomerase translocation. Since hnRNP A2* is capable of effectively unfolding the G-quadruplex, the impact of hnRNP A2* on telomerase processivity was examined using a modified TRAP assay. In a dilute solution, telomerase showed a relatively high processivity (FIGS. 3F, 7C, first lane). It has been reported previously that in the presence of PEG 200, a crowding agent widely used to mimic the molecularly crowded intracellular environment, the thermal stability of telomere G-quadruplex increases and the processivity of human telomerase decreases. Extension was realized in the presence of PEG200, and the processivity was significantly decreased (second lane), results of which was similar to the previous reports. hnRNP A2* stimulated telomerase processivity in the presence of PEG 200 (third lane), but POT1 did not (fourth lane). Because both hnRNP A2* and POT1 can disrupt G-quadruplex, this difference may reflect the fact that hnRNP A2* exposes a free 3' end when it binds to telomeric DNA, but POT1 does not.

hnRNP A2* Localizes to the Nuclear Matrix and Associates with Telomerase at telomeres and in Cajal bodies In Vivo.

The protein region encoded by exons 7-9 in hnRNP A2, which is missing from hnRNP A2*, is entirely hydrophilic. As a result, hnRNP A2* is more hydrophobic than hnRNP A2. hnRNP A2 localizes predominantly to the nucleoplasm, whereas hnRNP A2* localizes exclusively to the nuclear matrix proved by Western blot. This suggests that hnRNP A2 and hnRNP A2* have distinct cellular functions.

Figures 4A, 4B:
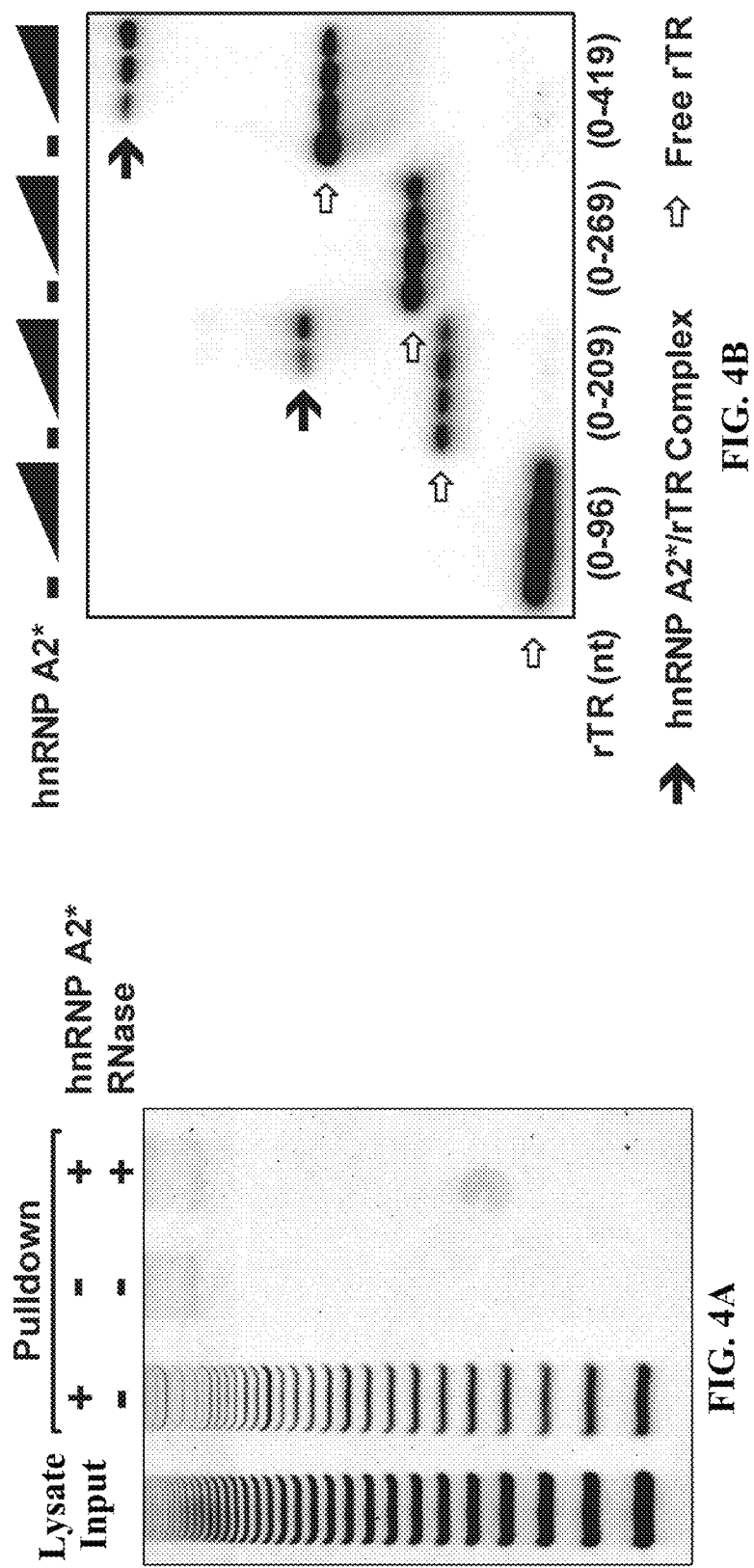
FIGS. 4A, 4B, and 4C show that hnRNP A2* interacts with telomerase both in vitro and in vivo. In particular.
Figure 9A:
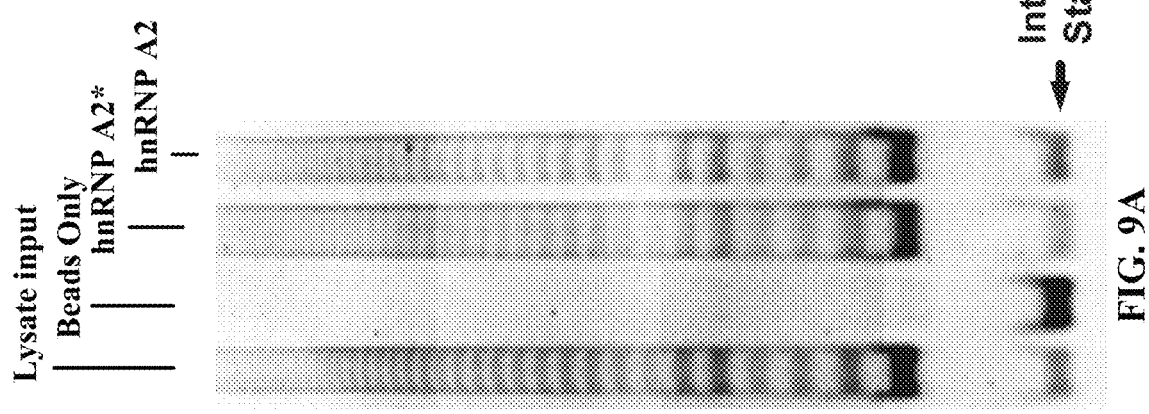
FIG. 9A shows the detection of telomerase activity from rat cells bound to hnRNP A2 protein fixed on a nickel shot.
Figure 8B:
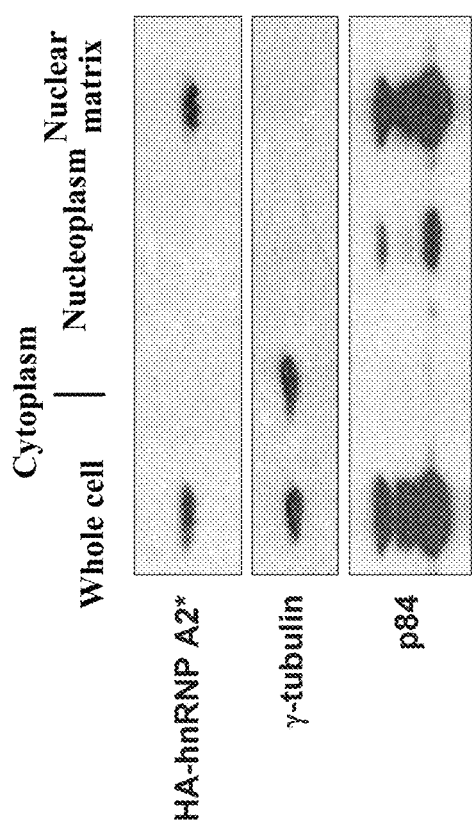
FIG. 8B shows protein hybridization detection of hnRNP A2* from different subcellular fractions in rat cells. HA-hnRNP A2* is expressed in the rat cells and anti-HA antibodies can detect the HA-hnRNP A2*. Proteins γ-tubulin and p84 are landmarks of cytoplasm and nuclear matrix, respectively, and are detected using different antibodies.
Figure 9B:
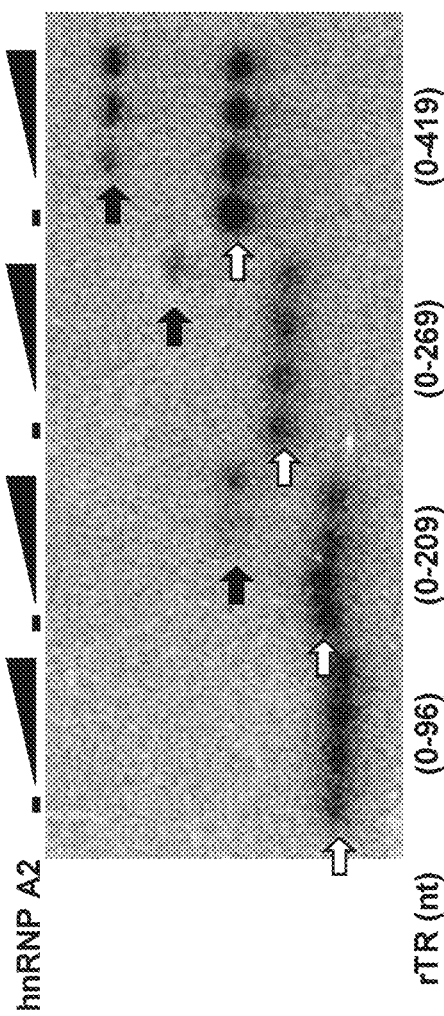
FIG. 9B shows that EMSA detects the binding capacity of hnRNP A2 to rat telomerase RNA with the increasing concentration gradient (0, 0.25, 0.5, 1 mM) of the protein. Solid arrows represent the complex of rTR and hnRNP A2*. Hollow arrows represent free rTR. The experiment conditions are the same as those in FIG. 4A and FIG. 4B.

Some proteins from the hnRNP family interact directly with telomerase, as well as with telomeric DNA, in vitro. It was founded that hnRNP A2* could pull-down telomerase activity from cell lysate (FIG. 9A) as did hnRNP A2, demonstrating that hnRNP A2* can physically interact with telomerase (FIG. 4A). In addition, hnRNP A2* directly binds the RNA component of rTR in vitro (FIG. 4B). This binding is dependent on the size/sequence and possibly the secondary structure of rTR. hnRNP A2 can also interact with the rat telomerase, but the working principle of hnRNP A2 is different from that of hnRNP A2, because hnRNP A2 binds to the 0-269 fragment of rTR (FIG. 9B), whereas hnRNP A2* does not (FIG. 4B).

Figure 10B:
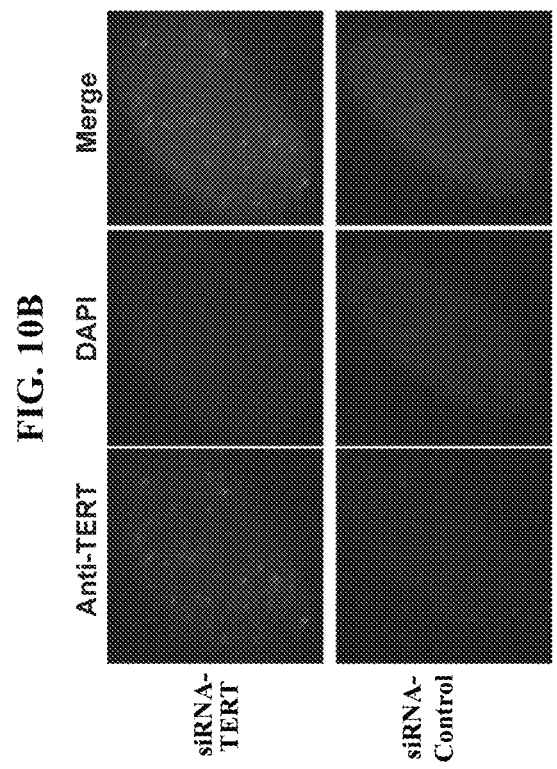
FIG. 10B shows anti-HA antibodies stain cultured rats cells expressing HA-hnRNP A2* (the upper part) and not expressing HA-TTAP using the immunofluorescence method.
Figure 10C:
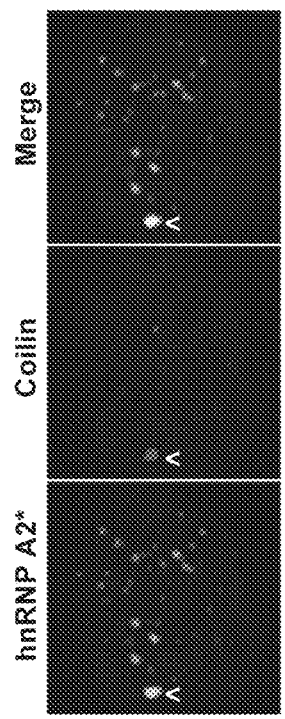
FIG. 10C shows the immunofluorescence method showing that the expression of the protein TERT in rats was inhibited by the TERT-interfered RNA. All images were collected from three independent experiments and shot within the same exposure time.
Figure 10A:
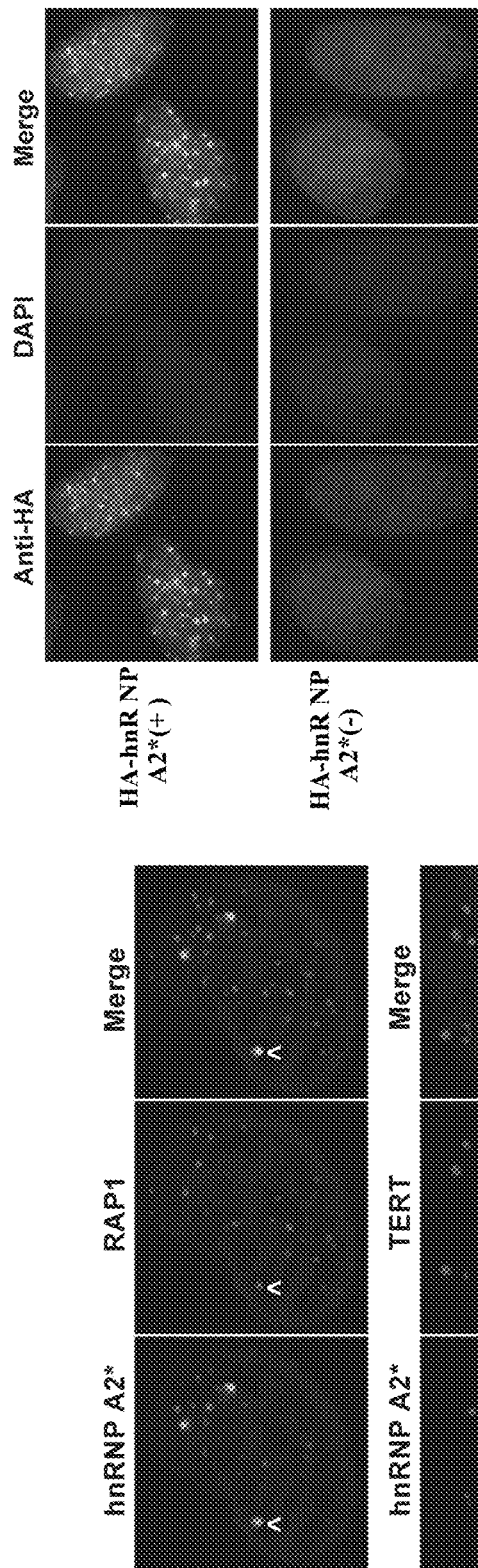
FIG. 10A shows the detection of the co-localization of hnRNP A2* and RAP1, TERT, Coilin in cultured rat cells using the immunofluorescence method. RAP1 and Coilin are marker molecules for telomere and Cajal body, respectively.

To examine whether hnRNP A2* interacts with telomeres and telomerase in vivo, HA-tagged hnRNP A2* was expressed in rat cells and immunofluorescence experiments were performed to localize the expressions. Consistent to experiment results in vitro, it was showed that a fraction of hnRNP A2* colocalized with RAP1 and with TERT (FIG. 10A, top and middle images). Fluorescence reduction of TERT by SiRNA (FIG. 10B) and selective staining of HA-hnRNP A2*-expressing cells (FIG. 10C) respectively corroborated that the antibody has specificity to the HA-hnRNP A2* and TERT. Interestingly, it was also founded that hnRNP A2* can also colocalize with Cajal bodies (FIG. 10A, bottom images). Because Cajal bodies are involved in the processing and positioning of telomerase at telomeres, it was hypothesized that hnRNP A2* may play a role in these processes.

Figure 4C:
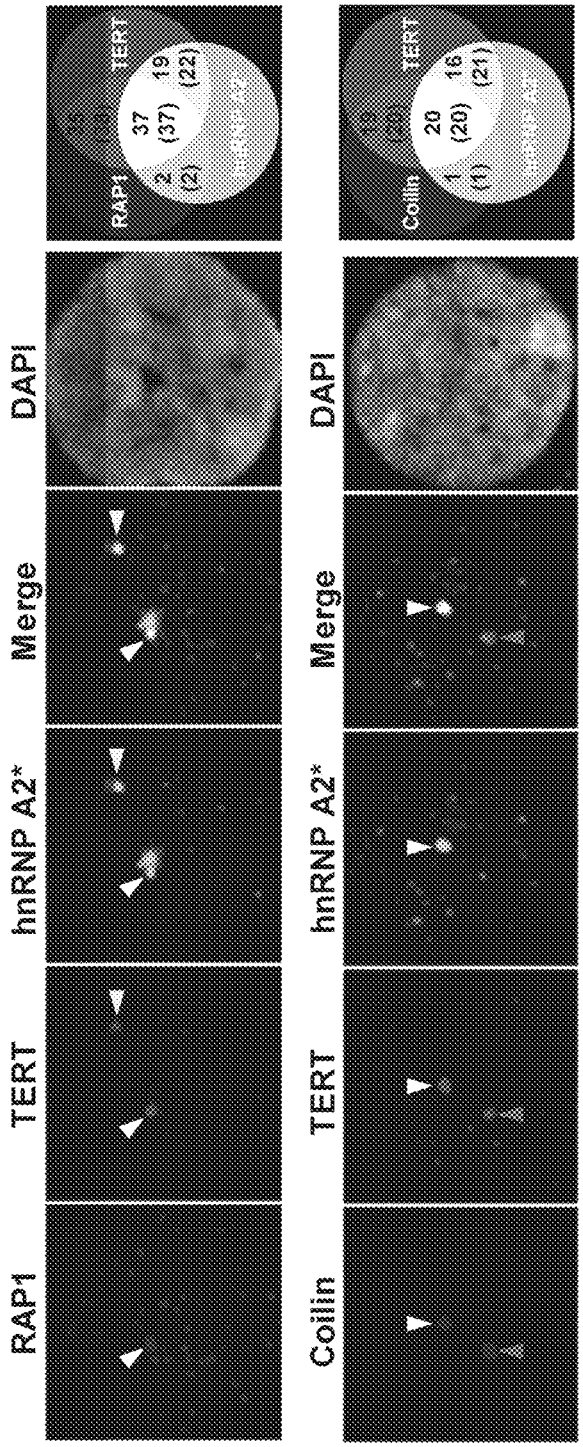
Figure 11A:
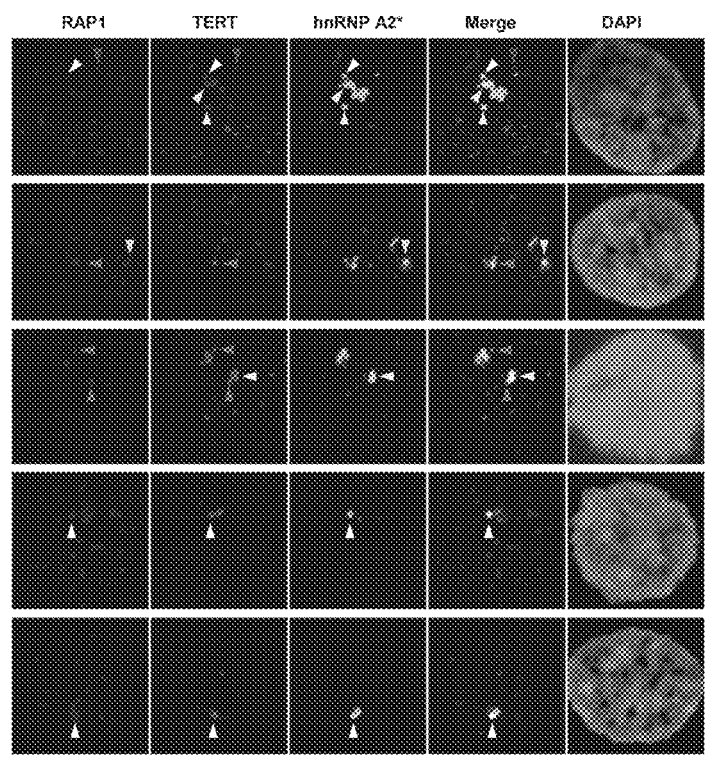
FIG. 11A shows the co-localization of hnRNP A2* with RAP1 and TERT in rat cells using the triple fluorescent labeling method. RAP1 is the marker molecule of telomere.
Figure 11B:
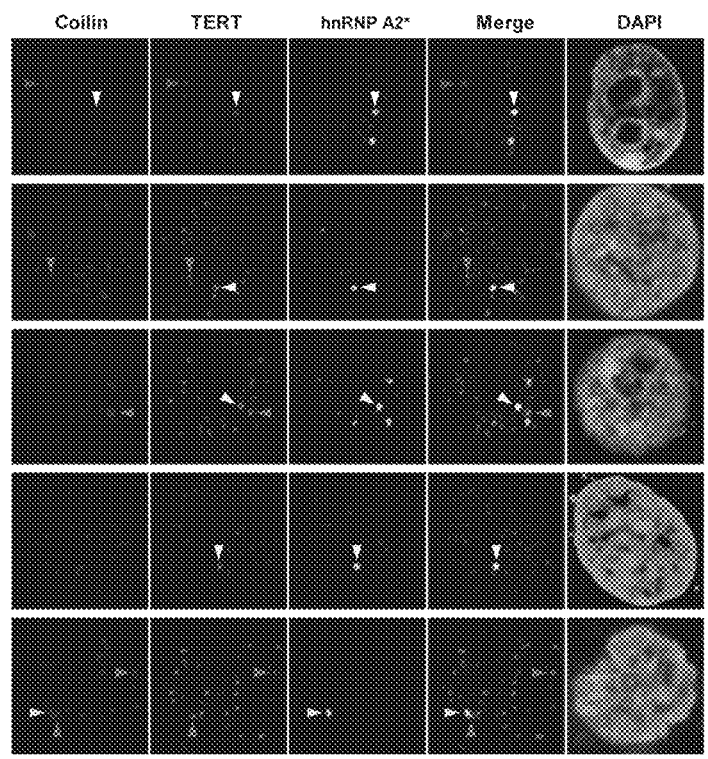
FIG. 11B shows the co-localization of hnRNP A2* with Coilin and TERT in rat cells using the triple fluorescent labeling method. Coilin is the marker molecule of Cajal body.

These interactions were further explored using three-color immunofluorescence. When hnRNP A2*, TERT, and telomere were detected at the same time, most hnRNP A2*/telomere foci was often positive for telomerase (FIG. 4C top images, FIG. 11A). Out of the 39 hnRNP A2*/RAP1 foci observed, 37 were also positive for telomerase (hnRNP A2*/RAP1/TERT foci). The hnRNP A2*/TERT/Cajal bodies forci also revealed a close relation between hnRNP A2* and the telomerase. Out of the 21 hnRNP A2*/Cajal bodies foci observed, 20 were found existing in the form of hnRNP A2*/Cajal bodies/TERT complexes (FIG. 4C bottom images, FIG. 11B). About half of the TERT at telomeres or in Cajal bodies was associated with hnRNP A2*. The prevalent colocalization of hnRNP A2* with telomerase at telomeres and in Cajal bodies strongly suggests that hnRNP A2* is a close partner of telomerase. It is possible that hnRNP A2* is assembled into the telomerase holoenzyme at Cajal bodies and delivered to telomeres. The finding that the binding of hnRNP A2* with rTR (FIG. 4B) involves the 3' region of rTR (269-419 nt), which contains the Cajal body box (CAB) motif responsible for its mobilization to the Cajal body, supports this hypothesis.

hnRNPA2* Expression Correlates with Telomerase Activity, and Overexpression of hnRNPA2* Increases Telomere Length In Vivo.

Figure 5A:
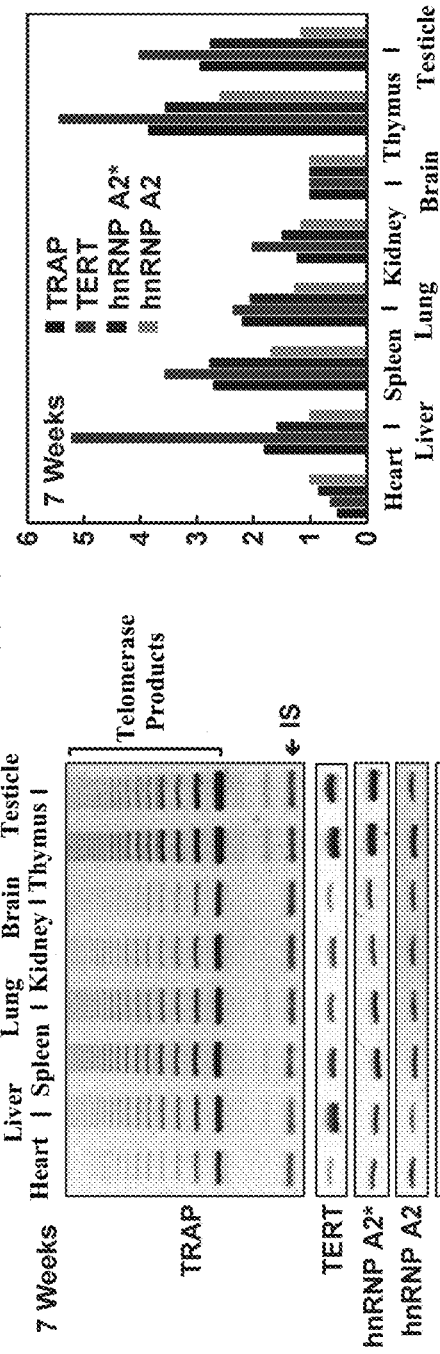
FIGS. 5A and 5B show in vivo correlation of hnRNP A2* expression with telomerase activity and telomere length. In particular.
Figures 12A, 12B:
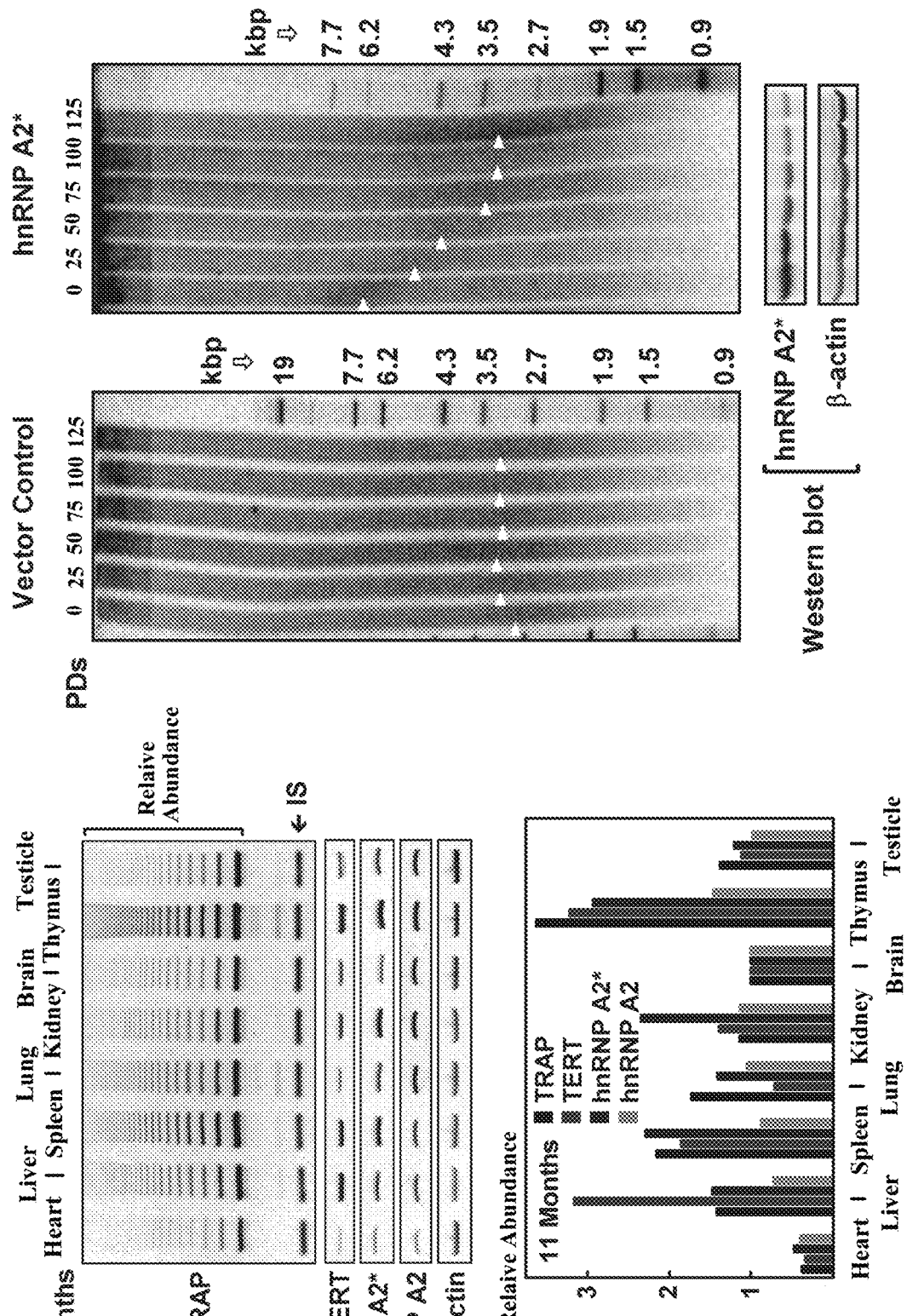
FIG. 12A shows the correlation between the expression quantity of hnRNP A2*, hnRNP A2, and TERT and the telomerase activity in 11 months old rats. The expression quantity of hnRNP A2*, hnRNP A2, and TERT were detected using RT-PCT method, and the telomerase activity was detected using TRAP method. The relative abundance was obtained first by normalizing the normal band intensity of actin and then normalizing the band intensity of brain tissue. IS is the internal reference.
FIG. 12B shows that the length of the telomere of rat cells increases with the increase of the overexpression of the hnRNP A2* protein. The density peak of each lane is indicated by white arrow. The expression of the hnRNP A2* protein is detected using the western blotting method, and other experiment conditions are the same as that in FIG. 5B.

Correlations between the expression of hnRNP A2* in vivo and the telomerase activity was also studied in the invention in order to corroborate the relation between hnRNP A2* and the telomerase. Amounts of hnRNP A2, hnRNP A2*, and TERT from rat tissues were determined by RT-PCR, and telomerase activity was quantified by TRAP (FIGS. 5A, 12A). Although telomerase activity did not correlate well with expression of TERT mRNA. For example, TERT mRNA is highly expressed in liver cells whereas the telomerase activity detected by TRAP is very low. But the telomerase activity well correlates with the expression of hnRNP A2*. This correlation implies an important role of hnRNP A2* for telomerase activity in vivo. On the contrary, this correlation is not presented between hnRNP A2* and the telomerase.

Figure 5B:
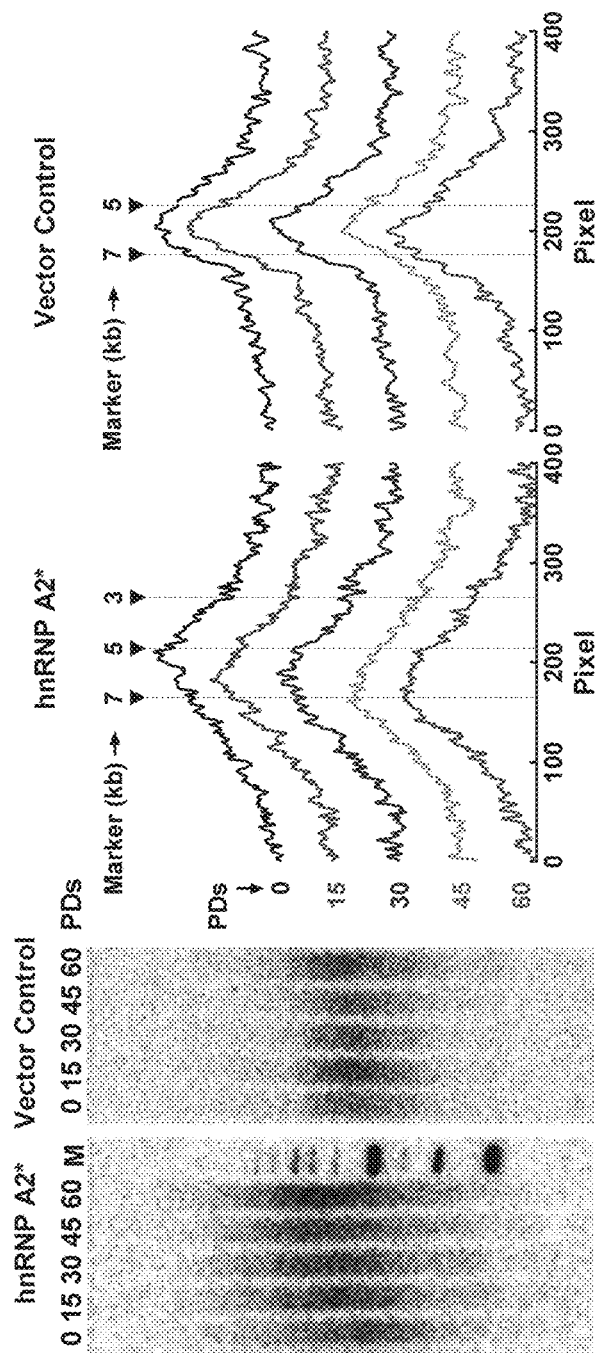

Because hnRNP A2* is expressed at a low level in human and rat cells, and because the abundance of hnRNP A2* correlates with higher telomerase activity in rat tissues (FIGS. 5A, 12A), it was predicted that overexpression of hnRNP A2* might correlate with increased telomere length. In fact, when hnRNP A2* was overexpressed in cultured HeLa and rat cells by retrovirus-mediated transfection, telomere length increased relative to control cells carrying empty vector (FIGS. 5B, 12B). Interestingly, the longer telomeres in the rat cells regressed over time, and in this context, subsequent telomere shortening correlated with a gradual decrease in hnRNP A2* expression (FIG. 12B bottom part). The dependence of the telomere length on the hnRNP A2* expression level further corroborates that hnRNP A2* is a positive factor for the telomerase to regulate the telomere extension.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A cDNA, comprising the nucleotide sequence represented by SEQ ID NO: 2.
2. A cDNA, comprising a nucleotide sequence encoding a complete protein, a protein fragment, a protein analogue, or a protein derivative each comprising the amino acid sequence represented by SEQ ID NO: 1.
3. The cDNA of claim 2, wherein the cDNA comprises the nucleotide sequence encoding the amino acid sequence represented by SEQ ID NO: 1.

* * * * *

SEQUENCE LISTING

```
<160> NUMBER OF SEQ ID NOS: 49

<210> SEQ ID NO 1
<211> LENGTH: 253
<212> TYPE: PRT
<213> ORGANISM: Artificial Sequence
<220> FEATURE:
<223> OTHER INFORMATION: Fully synthetic

<400> SEQUENCE: 1

Met Glu Arg Glu Lys Glu Gln Phe Arg Lys Leu Phe Ile Gly Gly Leu
1               5                   10                  15

Ser Phe Glu Thr Thr Glu Glu Ser Leu Arg Asn Tyr Tyr Glu Gln Trp
            20                  25                  30

Gly Lys Leu Thr Asp Cys Val Val Met Arg Asp Pro Ala Ser Lys Arg
        35                  40                  45

Ser Arg Gly Phe Gly Phe Val Thr Phe Ser Ser Met Ala Glu Val Asp
    50                  55                  60

Ala Ala Met Ala Ala Arg Pro His Ser Ile Asp Gly Arg Val Val Glu
```

```
                65                  70                  75                  80
Pro Lys Arg Ala Val Ala Arg Glu Gly Ser Gly Lys Pro Gly Ala His
                    85                  90                  95

Val Thr Val Lys Lys Leu Phe Val Gly Gly Ile Lys Glu Asp Thr Glu
                100                 105                 110

Glu His His Leu Arg Asp Tyr Phe Glu Glu Tyr Gly Lys Ile Asp Thr
                115                 120                 125

Ile Glu Ile Ile Thr Asp Arg Gln Ser Gly Lys Lys Arg Gly Phe Gly
    130                 135                 140

Phe Val Thr Phe Asp Asp His Asp Pro Val Asp Lys Ile Val Leu Gln
145                 150                 155                 160

Lys Tyr His Thr Ile Asn Gly His Asn Ala Glu Val Arg Lys Ala Leu
                165                 170                 175

Ser Arg Gln Glu Met Gln Glu Val Gln Ser Ser Arg Ser Gly Arg Gly
                180                 185                 190

Gly Asn Tyr Gly Ser Gly Asn Tyr Asn Asp Phe Gly Asn Tyr Asn Gln
            195                 200                 205

Gln Pro Ser Asn Tyr Gly Pro Met Lys Ser Gly Asn Phe Gly Gly Ser
    210                 215                 220

Arg Asn Met Gly Gly Pro Tyr Gly Gly Gly Asn Tyr Gly Pro Gly Gly
225                 230                 235                 240

Ser Gly Gly Ser Gly Gly Tyr Gly Gly Arg Ser Arg Tyr
                245                 250

<210> SEQ ID NO 2
<211> LENGTH: 762
<212> TYPE: DNA
<213> ORGANISM: Artificial Sequence
<220> FEATURE:
<223> OTHER INFORMATION: Fully synthetic

<400> SEQUENCE: 2
atggagagag aaaaggaaca gttccgtaag ctctttattg gtggcttaag ctttgaaacc      60
acagaagaaa gtttgaggaa ctactacgaa caatggggaa agcttacaga ctgtgtggta     120
atgagggatc ctgcaagcaa aagatcaaga ggatttggtt ttgtaacttt ttcatccatg     180
gctgaggttg atgctgccat ggctgcaaga cctcattcaa ttgatgggag agtagttgag     240
ccaaaacgtg ctgtagcaag agaggaatct ggaaaaccag gggctcatgt aactgtgaag     300
aagctgtttg ttggcggaat taagaagat actgaggaac atcaccttag agattacttt     360
gaggaatatg gaaaaattga taccattgag ataattactg ataggcagtc tggaaagaaa     420
agaggctttg gctttgttac ttttgatgac catgatcctg tggataaaat cgtattgcag     480
aaataccata ccatcaatgg tcataatgca gaagtaagaa aggctttgtc tagacaagaa     540
atgcaggaag ttcagagttc taggagtgga agaggaggca ttatggaag tggaaattac      600 aatgatttg gaaattataa ccagcaacct tctaactacg gtccaatgaa gagtggaaac      660
tttggtggta gcaggaacat gggggggacca tatggtggag gaaactatgg tccaggaggc     720
agtggaggaa gtgggggtta tggtggagg agccgatact ga                          762

<210> SEQ ID NO 3
<211> LENGTH: 341
<212> TYPE: PRT
<213> ORGANISM: Artificial Sequence
<220> FEATURE:
<223> OTHER INFORMATION: Fully synthetic
```

<400> SEQUENCE: 3

```
Met Glu Arg Glu Lys Glu Gln Phe Arg Lys Leu Phe Ile Gly Gly Leu
1               5                   10                  15

Ser Phe Glu Thr Thr Glu Glu Ser Leu Arg Asn Tyr Tyr Glu Gln Trp
            20                  25                  30

Gly Lys Leu Thr Asp Cys Val Val Met Arg Asp Pro Ala Ser Lys Arg
        35                  40                  45

Ser Arg Gly Phe Gly Phe Val Thr Phe Ser Ser Met Ala Glu Val Asp
50                  55                  60

Ala Ala Met Ala Ala Arg Pro His Ser Ile Asp Gly Arg Val Val Glu
65                  70                  75                  80

Pro Lys Arg Ala Val Ala Arg Glu Glu Ser Gly Lys Pro Gly Ala His
                85                  90                  95

Val Thr Val Lys Lys Leu Phe Val Gly Gly Ile Lys Glu Asp Thr Glu
            100                 105                 110

Glu His His Leu Arg Asp Tyr Phe Glu Glu Tyr Gly Lys Ile Asp Thr
        115                 120                 125

Ile Glu Ile Ile Thr Asp Arg Gln Ser Gly Lys Lys Arg Gly Phe Gly
130                 135                 140

Phe Val Thr Phe Asp Asp His Asp Pro Val Asp Lys Ile Val Leu Gln
145                 150                 155                 160

Lys Tyr His Thr Ile Asn Gly His Asn Ala Glu Val Arg Lys Ala Leu
                165                 170                 175

Ser Arg Gln Glu Met Gln Glu Val Gln Ser Ser Arg Ser Gly Arg Gly
            180                 185                 190

Gly Asn Phe Gly Phe Gly Asp Ser Arg Gly Gly Gly Asn Phe Gly
        195                 200                 205

Pro Gly Pro Gly Ser Asn Phe Arg Gly Gly Ser Asp Gly Tyr Gly Ser
210                 215                 220

Gly Arg Gly Phe Gly Asp Gly Tyr Asn Gly Tyr Gly Gly Gly Pro Gly
225                 230                 235                 240

Gly Gly Asn Phe Gly Gly Ser Pro Gly Tyr Gly Gly Gly Arg Gly Gly
                245                 250                 255

Tyr Gly Gly Gly Gly Pro Gly Tyr Gly Asn Gln Gly Gly Gly Tyr Gly
            260                 265                 270

Gly Gly Tyr Asp Asn Tyr Gly Gly Gly Asn Tyr Gly Ser Gly Asn Tyr
        275                 280                 285

Asn Asp Phe Gly Asn Tyr Asn Gln Gln Pro Ser Asn Tyr Gly Pro Met
290                 295                 300

Lys Ser Gly Asn Phe Gly Gly Ser Arg Asn Met Gly Gly Pro Tyr Gly
305                 310                 315                 320

Gly Gly Asn Tyr Gly Pro Gly Gly Ser Gly Ser Gly Gly Tyr Gly
                325                 330                 335

Gly Arg Ser Arg Tyr
            340
```

<210> SEQ ID NO 4
<211> LENGTH: 16
<212> TYPE: DNA
<213> ORGANISM: Artificial Sequence
<220> FEATURE:
<223> OTHER INFORMATION: Fully synthetic

<400> SEQUENCE: 4
ttagggttag ggttag                                                      16

```
<210> SEQ ID NO 5
<211> LENGTH: 15
<212> TYPE: DNA
<213> ORGANISM: Artificial Sequence
<220> FEATURE:
<223> OTHER INFORMATION: Fully synthetic

<400> SEQUENCE: 5
tagggttagg gttag                                                              15

<210> SEQ ID NO 6
<211> LENGTH: 14
<212> TYPE: DNA
<213> ORGANISM: Artificial Sequence
<220> FEATURE:
<223> OTHER INFORMATION: Fully synthetic

<400> SEQUENCE: 6
agggttaggg ttag                                                               14

<210> SEQ ID NO 7
<211> LENGTH: 13
<212> TYPE: DNA
<213> ORGANISM: Artificial Sequence
<220> FEATURE:
<223> OTHER INFORMATION: Fully synthetic

<400> SEQUENCE: 7
gggttagggt tag                                                                13

<210> SEQ ID NO 8
<211> LENGTH: 18
<212> TYPE: DNA
<213> ORGANISM: Artificial Sequence
<220> FEATURE:
<223> OTHER INFORMATION: Fully synthetic

<400> SEQUENCE: 8
ttagggttag ggttaggg                                                           18

<210> SEQ ID NO 9
<211> LENGTH: 14
<212> TYPE: DNA
<213> ORGANISM: Artificial Sequence
<220> FEATURE:
<223> OTHER INFORMATION: Fully synthetic

<400> SEQUENCE: 9
tagggttagg gtta                                                               14

<210> SEQ ID NO 10
<211> LENGTH: 13
<212> TYPE: DNA
<213> ORGANISM: Artificial Sequence
<220> FEATURE:
<223> OTHER INFORMATION: Fully synthetic

<400> SEQUENCE: 10
tagggttagg gtt                                                                13

<210> SEQ ID NO 11
<211> LENGTH: 12
<212> TYPE: DNA
<213> ORGANISM: Artificial Sequence
<220> FEATURE:
```

```
<223> OTHER INFORMATION: Fully synthetic

<400> SEQUENCE: 11
tagggttagg gt                                                                12

<210> SEQ ID NO 12
<211> LENGTH: 11
<212> TYPE: DNA
<213> ORGANISM: Artificial Sequence
<220> FEATURE:
<223> OTHER INFORMATION: Fully synthetic

<400> SEQUENCE: 12
tagggttagg g                                                                 11

<210> SEQ ID NO 13
<211> LENGTH: 10
<212> TYPE: DNA
<213> ORGANISM: Artificial Sequence
<220> FEATURE:
<223> OTHER INFORMATION: Fully synthetic

<400> SEQUENCE: 13
tagggttagg                                                                   10

<210> SEQ ID NO 14
<211> LENGTH: 22
<212> TYPE: DNA
<213> ORGANISM: Artificial Sequence
<220> FEATURE:
<223> OTHER INFORMATION: Fully synthetic

<400> SEQUENCE: 14
ttagggttag ggttagggtt ag                                                     22

<210> SEQ ID NO 15
<211> LENGTH: 22
<212> TYPE: DNA
<213> ORGANISM: Artificial Sequence
<220> FEATURE:
<223> OTHER INFORMATION: Fully synthetic

<400> SEQUENCE: 15
ttacggttag ggttagggtt ag                                                     22

<210> SEQ ID NO 16
<211> LENGTH: 22
<212> TYPE: DNA
<213> ORGANISM: Artificial Sequence
<220> FEATURE:
<223> OTHER INFORMATION: Fully synthetic

<400> SEQUENCE: 16
ttagggttag ggttagcgtt ag                                                     22

<210> SEQ ID NO 17
<211> LENGTH: 22
<212> TYPE: DNA
<213> ORGANISM: Artificial Sequence
<220> FEATURE:
<223> OTHER INFORMATION: Fully synthetic

<400> SEQUENCE: 17
ttacggttag cgttacggtt ag                                                     22
```

```
<210> SEQ ID NO 18
<211> LENGTH: 28
<212> TYPE: DNA
<213> ORGANISM: Artificial Sequence
<220> FEATURE:
<223> OTHER INFORMATION: Fully synthetic

<400> SEQUENCE: 18
ttagggttag ggttagggtt agggttag                                          28

<210> SEQ ID NO 19
<211> LENGTH: 16
<212> TYPE: DNA
<213> ORGANISM: Artificial Sequence
<220> FEATURE:
<223> OTHER INFORMATION: Fully synthetic

<400> SEQUENCE: 19
tttgggttag ggttag                                                       16

<210> SEQ ID NO 20
<211> LENGTH: 16
<212> TYPE: DNA
<213> ORGANISM: Artificial Sequence
<220> FEATURE:
<223> OTHER INFORMATION: Fully synthetic

<400> SEQUENCE: 20
ttagggttag cgttag                                                       16

<210> SEQ ID NO 21
<211> LENGTH: 16
<212> TYPE: DNA
<213> ORGANISM: Artificial Sequence
<220> FEATURE:
<223> OTHER INFORMATION: Fully synthetic

<400> SEQUENCE: 21
tttgggttag cgttag                                                       16

<210> SEQ ID NO 22
<211> LENGTH: 15
<212> TYPE: DNA
<213> ORGANISM: Artificial Sequence
<220> FEATURE:
<223> OTHER INFORMATION: Fully synthetic

<400> SEQUENCE: 22
tagggttagg gttag                                                        15

<210> SEQ ID NO 23
<211> LENGTH: 26
<212> TYPE: DNA
<213> ORGANISM: Artificial Sequence
<220> FEATURE:
<223> OTHER INFORMATION: Fully synthetic

<400> SEQUENCE: 23
tagctagcat ggagagagaa aaggaa                                            26

<210> SEQ ID NO 24
<211> LENGTH: 27
<212> TYPE: DNA
<213> ORGANISM: Artificial Sequence
<220> FEATURE:
<223> OTHER INFORMATION: Fully synthetic
```

```
<400> SEQUENCE: 24
aagagctctc aatatcggct ccttcca                                           27

<210> SEQ ID NO 25
<211> LENGTH: 18
<212> TYPE: DNA
<213> ORGANISM: Artificial Sequence
<220> FEATURE:
<223> OTHER INFORMATION: Fully synthetic

<400> SEQUENCE: 25
aatccgtcga gcagagtt                                                     18

<210> SEQ ID NO 26
<211> LENGTH: 25
<212> TYPE: DNA
<213> ORGANISM: Artificial Sequence
<220> FEATURE:
<223> OTHER INFORMATION: Fully synthetic

<400> SEQUENCE: 26
gggctagggc tagggctagg gagtt                                             25

<210> SEQ ID NO 27
<211> LENGTH: 36
<212> TYPE: DNA
<213> ORGANISM: Artificial Sequence
<220> FEATURE:
<223> OTHER INFORMATION: Fully synthetic

<400> SEQUENCE: 27
aatccgtcga gcagagttaa aaggccgaga agcgat                                 36

<210> SEQ ID NO 28
<211> LENGTH: 18
<212> TYPE: DNA
<213> ORGANISM: Artificial Sequence
<220> FEATURE:
<223> OTHER INFORMATION: Fully synthetic

<400> SEQUENCE: 28
atcgcttctc ggccttttt                                                    18

<210> SEQ ID NO 29
<211> LENGTH: 43
<212> TYPE: DNA
<213> ORGANISM: Artificial Sequence
<220> FEATURE:
<223> OTHER INFORMATION: Fully synthetic

<400> SEQUENCE: 29
gggctagggc tagggctagg gagttaagcg gccgagaagc gag                         43

<210> SEQ ID NO 30
<211> LENGTH: 18
<212> TYPE: DNA
<213> ORGANISM: Artificial Sequence
<220> FEATURE:
<223> OTHER INFORMATION: Fully synthetic

<400> SEQUENCE: 30
ctcgcttctc ggccgctt                                                     18

<210> SEQ ID NO 31
<211> LENGTH: 30
```

<212> TYPE: DNA
<213> ORGANISM: Artificial Sequence
<220> FEATURE:
<223> OTHER INFORMATION: Fully synthetic

<400> SEQUENCE: 31
gcgcggctta cccttaccct taccctaacc                                      30

<210> SEQ ID NO 32
<211> LENGTH: 27
<212> TYPE: DNA
<213> ORGANISM: Artificial Sequence
<220> FEATURE:
<223> OTHER INFORMATION: Fully synthetic

<400> SEQUENCE: 32
gtgcccttac ccttaccctt accctaa                                         27

<210> SEQ ID NO 33
<211> LENGTH: 38
<212> TYPE: DNA
<213> ORGANISM: Artificial Sequence
<220> FEATURE:
<223> OTHER INFORMATION: Fully synthetic

<400> SEQUENCE: 33
agcatccgtc gagcagagtt aaaaggccga gaagcgat                             38

<210> SEQ ID NO 34
<211> LENGTH: 33
<212> TYPE: DNA
<213> ORGANISM: Artificial Sequence
<220> FEATURE:
<223> OTHER INFORMATION: Fully synthetic

<400> SEQUENCE: 34
gatggtacca tggagagaga aaaggaacag ttc                                  33

<210> SEQ ID NO 35
<211> LENGTH: 33
<212> TYPE: DNA
<213> ORGANISM: Artificial Sequence
<220> FEATURE:
<223> OTHER INFORMATION: Fully synthetic

<400> SEQUENCE: 35
gacgaattca ttctcaatat cggctccttc cac                                  33

<210> SEQ ID NO 36
<211> LENGTH: 21
<212> TYPE: DNA
<213> ORGANISM: Artificial Sequence
<220> FEATURE:
<223> OTHER INFORMATION: Fully synthetic

<400> SEQUENCE: 36
taatacgagt cactataggg a                                               21

<210> SEQ ID NO 37
<211> LENGTH: 21
<212> TYPE: DNA
<213> ORGANISM: Artificial Sequence
<220> FEATURE:
<223> OTHER INFORMATION: Fully synthetic

<400> SEQUENCE: 37

```
gggttagggt tagggttagg g                                            21
```

<210> SEQ ID NO 38
<211> LENGTH: 21
<212> TYPE: DNA
<213> ORGANISM: Artificial Sequence
<220> FEATURE:
<223> OTHER INFORMATION: Fully synthetic

<400> SEQUENCE: 38

```
ccctaacccT aaccctaacc c                                            21
```

<210> SEQ ID NO 39
<211> LENGTH: 19
<212> TYPE: DNA
<213> ORGANISM: Artificial Sequence
<220> FEATURE:
<223> OTHER INFORMATION: Fully synthetic

<400> SEQUENCE: 39

```
gccagcatgt taggaagaa                                               19
```

<210> SEQ ID NO 40
<211> LENGTH: 6
<212> TYPE: PRT
<213> ORGANISM: Artificial Sequence
<220> FEATURE:
<223> OTHER INFORMATION: Fully synthetic

<400> SEQUENCE: 40

```
Val Val Glu Pro Lys Arg
1               5
```

<210> SEQ ID NO 41
<211> LENGTH: 8
<212> TYPE: PRT
<213> ORGANISM: Artificial Sequence
<220> FEATURE:
<223> OTHER INFORMATION: Fully synthetic

<400> SEQUENCE: 41

```
Ser Gly Asn Phe Gly Gly Ser Arg
1               5
```

<210> SEQ ID NO 42
<211> LENGTH: 8
<212> TYPE: PRT
<213> ORGANISM: Artificial Sequence
<220> FEATURE:
<223> OTHER INFORMATION: Fully synthetic

<400> SEQUENCE: 42

```
Asn Tyr Tyr Glu Gln Trp Gly Lys
1               5
```

<210> SEQ ID NO 43
<211> LENGTH: 8
<212> TYPE: PRT
<213> ORGANISM: Artificial Sequence
<220> FEATURE:
<223> OTHER INFORMATION: Fully synthetic

<400> SEQUENCE: 43

```
Leu Thr Asp Cys Val Val Met Arg
1               5
```

```
<210> SEQ ID NO 44
<211> LENGTH: 10
<212> TYPE: PRT
<213> ORGANISM: Artificial Sequence
<220> FEATURE:
<223> OTHER INFORMATION: Fully synthetic

<400> SEQUENCE: 44

Ile Asp Thr Ile Glu Ile Ile Thr Asp Arg
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Fully synthetic

<400> SEQUENCE: 45

Glu Glu Ser Gly Lys Pro Gly Ala His Val Thr Val Lys
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Fully synthetic

<400> SEQUENCE: 46

Gly Phe Gly Phe Val Thr Phe Asp Asp His Asp Pro Val Asp Lys
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Fully synthetic

<400> SEQUENCE: 47

Leu Phe Ile Gly Gly Leu Ser Phe Glu Thr Thr Glu Glu Ser Leu Arg
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Fully synthetic

<400> SEQUENCE: 48

Leu Phe Val Gly Gly Ile Lys Glu Asp Thr Glu Glu His His Leu Arg
1               5                   10                  15

<210> SEQ ID NO 49
<211> LENGTH: 18
<212> TYPE: PRT
<213> ORGANISM: Artificial Sequence
<220> FEATURE:
<223> OTHER INFORMATION: Fully synthetic

<400> SEQUENCE: 49

Asp Tyr Phe Glu Glu Tyr Gly Lys Ile Asp Thr Ile Glu Ile Ile Thr
1               5                   10                  15

Asp Arg
```